United States Patent
Mills

(10) Patent No.: US 6,719,705 B2
(45) Date of Patent: Apr. 13, 2004

(54) DEVICE AND METHOD FOR NONINVASIVE CONTINUOUS DETERMINATION OF PHYSIOLOGIC CHARACTERISTICS

(76) Inventor: Alexander K. Mills, 7 Old Westbury La., Webster Groves, MO (US) 63119

( * ) Notice: Subject to any disclaimer, the term of this patent is extended or adjusted under 35 U.S.C. 154(b) by 0 days.

(21) Appl. No.: 10/196,474

(22) Filed: Jul. 15, 2002

(65) Prior Publication Data

US 2002/0188205 A1 Dec. 12, 2002

Related U.S. Application Data

(62) Division of application No. 09/684,104, filed on Oct. 6, 2000
(60) Provisional application No. 60/158,097, filed on Oct. 7, 2000.

(51) Int. Cl.[7] .................................................. A61B 5/02
(52) U.S. Cl. ........................ 600/526; 600/300; 600/301; 600/323; 600/324; 600/504; 600/507
(58) Field of Search ................................. 600/323, 324, 600/328, 322, 326, 481, 485, 500–504, 507, 526

(56) References Cited

U.S. PATENT DOCUMENTS

| | | | | |
|---|---|---|---|---|
| 4,676,253 A | * | 6/1987 | Newman et al. ............. | 600/506 |
| 5,218,962 A | * | 6/1993 | Mannheimer et al. ....... | 600/331 |
| 5,308,919 A | * | 5/1994 | Minnich ...................... | 600/320 |
| 5,743,268 A | * | 4/1998 | Kabal .......................... | 600/526 |
| 5,964,701 A | * | 10/1999 | Asada et al. ................. | 600/300 |
| 6,178,343 B1 | * | 1/2001 | Bindszus et al. ............ | 600/323 |
| 6,334,065 B1 | * | 12/2001 | Al-Ali et al. ................ | 600/323 |

* cited by examiner

Primary Examiner—Robert L. Nasser
Assistant Examiner—Patricia Mallari
(74) Attorney, Agent, or Firm—Francis Law Group

(57) ABSTRACT

The invention comprises devices for noninvasively monitoring physiological characteristics of a patient's blood. Generally, probes having radiation emitters and detectors are used to determine absorbance of blood within the patient's tissue to determine various blood parameters. The device also has either a position sensor for determining the position of the probe with respect to the patient's heart or a movement generator for altering the position of the probe with respect to the patient's heart. The invention also comprises methods for noninvasively monitoring the physiological characteristics. In one embodiemnt, induced positional changes create differential hydrostatic pressures to facilitate measurement of blood parameters by absorbance. In a second embodiment, delays in pulse arrival times in coupled organs or members on opposite sides of the body are measured to determine cardiac output. The two methods are such that they can advantageously be used together.

10 Claims, 17 Drawing Sheets

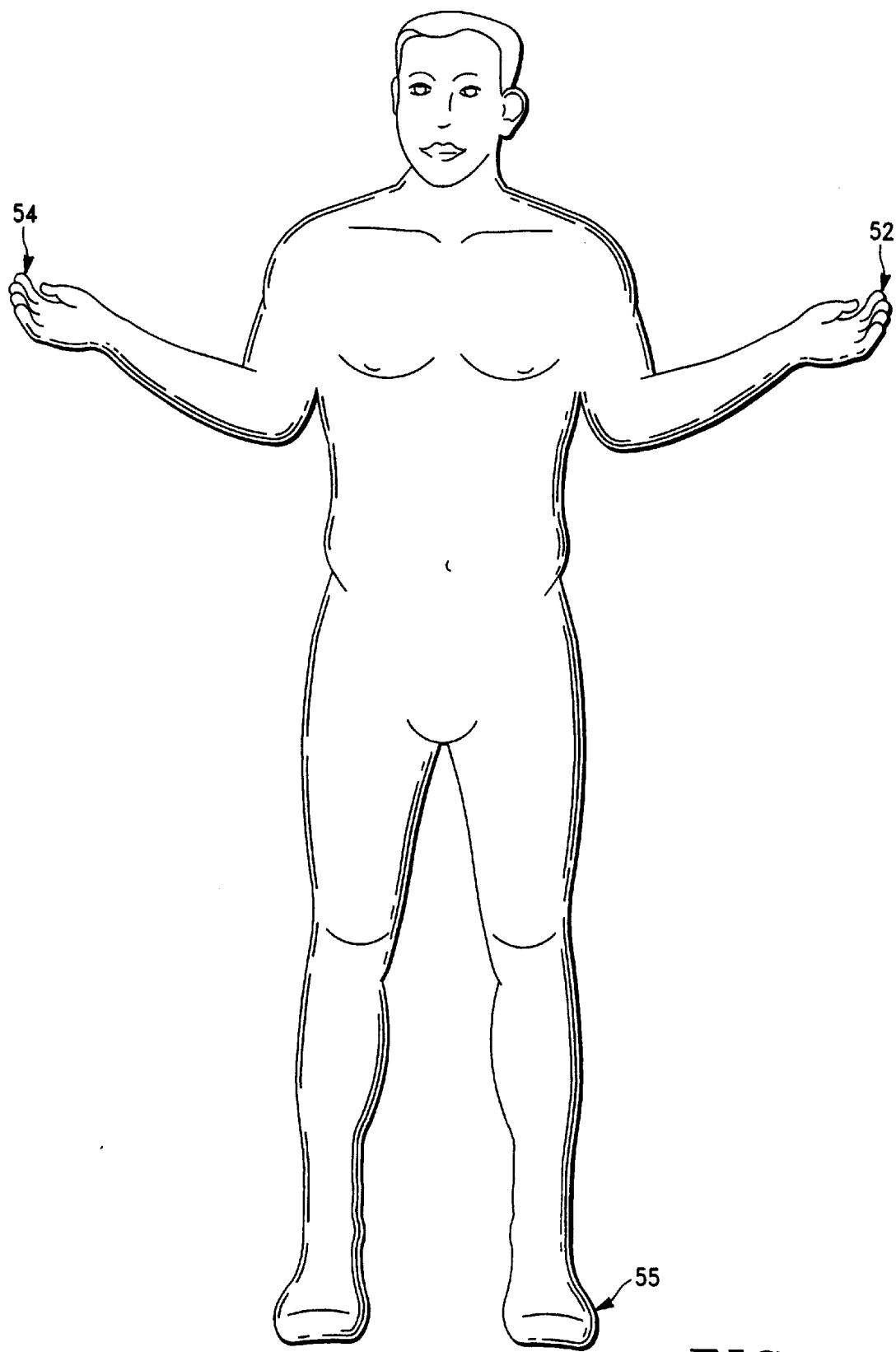
FIG.−18

DEVICE AND METHOD FOR NONINVASIVE CONTINUOUS DETERMINATION OF PHYSIOLOGIC CHARACTERISTICS

CROSS-REFERENCE TO RELATED APPLICATIONS

This is a division of application Ser. No. 09/684,104, filed Oct. 6, 2000 which claims benefit of Provisional Appl. Ser. No. 60/158,097, filed Oct. 7, 2000.

FIELD OF THE INVENTION

The present invention relates generally to noninvasive methods of quantitatively determining various physiologic parameters relating to cardiovascular and respiratory function. More particularly, the invention relates to a method and apparatus for continuous, noninvasive determination of: arterial blood pressure, venous pressure, arterial oxygen saturation, venous oxygen saturation, arterial pulse wave velocity, aortic pulse wave velocity, aortic pulse flow velocity, cardiac stroke volume, cardiac output, heart rate, and respiratory rate.

BACKGROUND OF THE INVENTION

Critically ill and seriously injured patients require constant care and attention. Doctors, nurses, and hospital technicians need a continuous flow of information about the many patients under their care. Heart rate and blood pressure measurements are two primary vital signs that indicate the health of patients under their care. When these two common indices of wellness fall below normal readings, a patient is usually in distress and requires immediate attention.

Dangerous conditions brought about by a cardio-vascular or pulmonary disease, severe trauma, or drug abuse may bring about a failure of the lungs and heart to supply the bloodstream with life-giving oxygen. Such a fatal deficiency can be detected by continually gauging the amount of hemoglobin in the bloodstream that is carrying oxygen. This third vital sign, which manifests oxygen saturation of the blood, is especially critical because a rapid decline in oxygen in the bloodstream is associated with increased risk of patient mortality.

It is well known that blood pressure can be directly measured by placing a fluid-filled catheter directly into the vessel and coupling this to an electro-mechanical transducer. This is the most accurate means, but has all the disadvantages of invasive measurement, including pain on insertion, risk of infection or disease transmission, risk of bleeding or thrombosis, and great expense. A further disadvantage is the creation of toxic medical waste (needle, gloves, skin dressing, etc).

Blood pressure measurement can also be measured indirectly using an occlusive cuff (with either auscultation or oscillometry to make the determination). This is the most common means of blood pressure measurement. Illustrative are U.S. Pat. Nos. 5,582,179, 5,048,533, 5,152,296 and 4,793,360.

A further occlusive cuff apparatus is disclosed in U.S. Pat. No. 5,766,130. According to the invention, the apparatus includes multiple "pressurized pneumatic cuffs" that are used to "plot blood pressure and/or volumetric blood flow wave forms from a plurality of separate digits and/or extremities of a patient so that circulatory parameters may be measured rapidly and recorded from a great number of the patient's digits or limbs".

Although commonly employed, the occlusive cuff also has numerous disadvantages, which include discomfort, intermittent readings, and poor reliability.

An additional means of determining blood pressure is through an assessment of "pulse wave velocity". Several prior art references disclose methods and/or apparatus employing such means. Illustrative is U.S. Pat. No. 5,649,543.

There are also several prior art references that disclose methods and/or apparatus for determining blood pressure through a "pulse wave amplitude" assessment Illustrative are U.S. Pat. Nos. 4,735,213, 4,872,461, 4,793,360, and 5,385,149.

Although most of the noted noninvasive blood pressure methods and apparatus, particularly the occlusive cuff, have been employed for many years by health care personnel, the conventional methods and apparatus have one major, common drawback—the need for separate calibration.

Accordingly, there is a need for noninvasive methods and devices for determining various physiological characteristics, such as central venous pressure and cardiac output, without separate calibration. There is also a similar need for noninvasive methods and devices for determining various blood parameters including pulse amplitude, pulse delay, pulse velocity, pulse contour, flow velocity and flow delay.

As will be appreciated by one having ordinary skill in the art, the present invention satisfies these and other needs.

SUMMARY OF THE INVENTION

The present invention includes a device for the noninvasive monitoring of a physiologic characteristic of a patient's blood. In one embodiment, the device comprises a tissue probe having a radiation emitter and a radiation detector configured to receive the radiation after absorbance through the patient's blood; a position sensor for determining the relative height of the probe compared to a level corresponding to the patient's heart; and a controller for computing the physiologic characteristic of the patient's blood based on the absorbance of the first wavelength of radiation and the relative height of the probe. The radiation emitters of the invention can utilize a single wavelength or a plurality of discrete wavelengths and may include visible light, infrared light, and ultraviolet light. The probes are adapted for use with hands, fingers, feet, toes, ears, earlobes, nares, lips, tongue and the like. Additional radiation emitters and detectors may also be used. Preferably, the probe further comprises ECG leads.

An alternative embodiment of the device of the invention comprises a tissue probe and controller in conjunction with a movement generator for inducing a position change of the probe with respect to a level corresponding to the patient's heart. Preferably, the movement generator induces a known position change of the probe and moves the probe to positions above and below a level corresponding to the patient's heart.

The invention also comprises method for determining a physiological characteristic of a patient's blood noninvasively. In one embodiment, absorbance characteristics of the blood are measured at varying positions relatively to the level of the patient's heart. By comparing blood parameters such as pulse amplitude, pulse velocity, pulse delay, pulse contour, flow velocity and flow delay to hydrostatic pressure differences induced by the position changes, characteristics such as arterial and central venous blood pressure and cardiac output can be determined. Alternatively, two probes are used to compute pulse delays between coupled tissues or opposing tissues.

The subject invention relates novel methods for noninvasive determination of physiologic characteristics. The first new and unique method and device utilizes changes in hydrostatic pressure induced by positional changes to facilitate measurements. A second new and unique method and device for noninvasive determination of cardiac output by measuring delays in pulse arrival times in coupled organs or members on opposite sides of the body is also described. The two methods are such that they can advantageously be used together.

By varying the hydrostatic pressure in an extremity, one can not only perform self-calibration for a blood pressure determination, but also change the pulse wave velocity and pulse propagation delay with respect to the opposite extremity. With this information, pulse wave velocity, and consequently flow wave velocity at the aortic root can be determined.

Similar techniques of varying hydrostatic pressure can be used to assess venous pressure and saturation. The technique of repetitious determinations made while altering position or other variables allows a multitude of additional analyses to be made. The determinations can be made intermittently or continuously.

Further objects of the invention are exemplified by the following potential applications:

(a1). A patient is anesthetized for a surgical procedure. Probes are attached to the index fingers of each hand, and a movement generator is placed on one arm. A complete set of vital signs and physiologic characteristics is generated continuously, including: arterial blood pressure, venous pressure, arterial oxygen saturation, venous oxygen saturation, arterial pulse wave velocity, aortic pulse wave velocity, aortic pulse flow velocity, cardiac stroke volume, cardiac output, heart rate, and respiratory rate. Other characteristics can be calculated if desired.

(a2). A patient is anesthetized for a cardiac surgical procedure. As access to the arms is difficult, probes are attached to the patient's temples. A complete set of vital signs and physiologic characteristics is continuously generated.

(a3). A patient is anesthetized for a cardiac surgical procedure; this time the procedure includes valvular repair or replacement. Since the cardiac output and other characteristics can be continuously computed, the adequacy of the surgical repair can be judged immediately.

(a4). As the number of endoscopic or minimally invasive cardiac surgical procedures is expected to increase, the demand for less invasive monitoring will also increase. The device described herein provides noninvasive, continuous monitoring of essentially all cardiovascular characteristics.

(a5). Cardiac catheterization procedures are often done on critically ill patients. As the procedures are usually relatively brief and accomplished without general anesthesia, invasive monitoring methods are often not desired despite the illness of the patients. The device described herein will provide the necessary monitoring that is typically provided by much more invasive, expensive, and time consuming monitors (a6). A patient is hospitalized in the intensive care unit of a hospital after a heart attack. Probes are attached to the index fingers of each hand, and a movement generator is placed on an arm or a leg. A complete set of vital signs and physiologic characteristics can be continuously generated. In addition, arrhythmias can be detected and diagnosed.

(a7). The patient noted above is now moved to a "stepdown" or telemetry unit from the intensive care unit. Because the device described herein eliminates the need for invasive monitoring lines, a complete set of vital signs and physiologic characteristics can still be continuously generated. As the patient has mobility of arms and legs, a movement generator is no longer needed, as the patient's spontaneous motion, even during sleep, will generate hydrostatic pressures in the limbs, allowing all computations to be made. In addition, the probes may be made wireless, and connected to a central nursing station by means of infrared or radio frequency communication.

(a8). The patient noted in applications 6 and 7 above is now moved to a regular hospital bed, and does not require continuous monitoring. However, vital signs can still be recorded by a technician moving the device from bedside to bedside on a cart. The device does not require highly trained nursing personnel to operate.

(a9). The patient noted in applications 6, 7, and 8 above has now been discharged from the hospital, and now presents to his physician's office for follow-up. The same device can be used in physician's offices, as it provides better care at lower cost.

(a10). Ambulances, emergency vehicles, and military vehicles can also employ this device as it is very simple to operate, and provides data that currently is impossible for them to obtain. In addition, the information can be transmitted to central stations where medical personnel are available for help and advice.

(a11). The device and methods of the invention will provide means of monitoring patients or checking vital signs for extended care facilities, nursing homes, and other health-related facilities (a12). Blood pressure screening clinics and drugstores will have a greatly improved means of determining patient's blood pressures and other vital signs. Airports and airplanes are able to purchase medical equipment, but often do not have personnel trained to operate the equipment. The device is simple and quick to operate.

(a13). The patient noted in applications 6 through 9 above can also monitor his heart disease and health care at home. The operation of the device is straightforward enough to be used by the layman with minimal instruction, and inexpensive enough for personal home use. The patient can measure his cardiovascular characteristics daily, or as frequently as he and his physician desire. A communication means, such as a modem, can easily be incorporated into the device. This, with appropriate software and support, would allow essentially instantaneous communication with a physician's office, clinic, or hospital. In addition, a permanent record can be made and stored electronically. If desired, the device could automatically "sign on" to the Internet or other network, and link to the appropriate website or other address. The ability to participate more fully in their own health care will improve the welfare of individuals.

(a14). The patient of above presents to the emergency room of a hospital with chest pain. The ER physician can access, via the Internet or other means, the patient's vital sign history, including ECG. This allows the physician to determine if abnormalities are new or chronic. Changes, such as dysrhythmias, can be identified as to when they first occurred, perhaps to within a time frame of hours or less.

(a15). People without diagnosed cardiovascular disease can use the device to allow themselves to participate in their own health care. This will allow virtually immediate diagnosis of any problems, allowing early intervention. In addition, a permanent record can be created if desired.

(a16). The device will impact fitness and physical training for everyone from lay people to military personnel to professional athletes.

(a17). The device can be employed in the diagnosis and management of peripheral vascular disease. Measurement of pulse wave velocity in the extremities, and particular differential pulse wave velocities in the lower extremities, can be used to diagnose peripheral vascular disease. Since measurements are real time and continuous, they can also be used in management. For example, if balloon angioplasty of an artery is performed, the clinician can tell immediately if flow has improved. In the case of angioplasty of coronary arteries, the clinician can follow cardiac characteristics on a beat-by-beat basis.

(a18). In addition to peripheral vascular disease, other diseases, such as abdominal aortic aneurysm, can be diagnosed and managed. Changes in pulse wave velocity and waveform can be followed for years if desired.

(a19). Some of the most important potential uses of the device relate to the health care of neonates and young children. For these patients, the measurement of common characteristics such as blood pressure can be difficult even for highly trained personnel in well-equipped facilities. The simple placement of probes on fingers will alleviate this. The device will also allow noninvasive diagnosis of congenital cardiac defects and anomalies. Analysis of differential pulse wave velocity and blood pressure will allow rapid, accurate, and specific diagnosis of many disorders, including Tetralogy of Fallot and transposition of the great vessels. The ability to distinguish both arterial and venous saturations and pressures will allow diagnosis of patent ductus arteriosus, truncus arteriosus, atrial septal defect, and ventricular septal defect. Differential arm and leg pulse wave velocities and pressures will confirm diagnosis of coarctation of the aorta. Because of its continuous measurements, the device can be used for only for diagnosis but confirmation of adequacy of repair, including intraoperatively. As the device is inexpensive and easy to operate, it may become a screening tool for newborns and infants.

(a20). The device can be used in conjunction with intra-aortic balloon pump (IABP) counterpulsation. Beat-by-beat analysis of effectiveness and ability to wean from counterpulsation can be made.

(a21). The device can be used in conjunction with placement of cardiac pacemakers, to set proper rate and timing intervals. In addition, efficacy of pacemakers can be checked as frequently as desired, and scheduling of reprogramming or replacement made automatically.

(a22). It is straightforward to incorporate other devices, such as the electroencephalogram (EEG) or electromyogram (EMG), into probes of the invention. As a general-purpose monitor, the device will invite the addition of specialized add-ons.

(a23). Many enhancements are included in the invention. For example, addition of chest (horizontal) leads allows full diagnostic ECGs to be performed.

(a24). Under some circumstances, such as severe hypotension, the pulse cannot be identified in the periphery. In such cases, many of the determinations claimed herein cannot be made. However, the ability of the device to identify venous blood can still give important information.

(a25). Forces other than gravity can be used. In a microgravity environment such as a space station orbiting the Earth, a device such as the one described could be constructed to perform all indicated determinations using acceleration caused by movement in place of gravitational acceleration.

(a26). As mentioned in the examples above, an anticipated use is in the field of home health care, with the possibility of automatic sign-on and direction to a website. As the user is already participating in his or her health care, the extension of providing access to related health or other information via the Internet® is a natural one.

(a27). A verification means, such as fingerprint scanning, can be incorporated into a personal-use device, to ensure that any medical information gathered belonged to the individual using the device.

(a28). The device will be used in conjunction with the Penaz technique or other methods, such as calibration with a cuff or other means, as desired.

BRIEF DESCRIPTION OF THE FIGURES

Further features and advantages will become apparent from the following and more particular description of the preferred embodiments of the invention, as illustrated in the accompanying drawings, and in which like referenced characters generally refer to the same parts or elements throughout the views, and in which:

FIG. 18 shows an embodiment of the invention with probes placed on opposite fingers and on a toe;

DETAILED DESCRIPTION OF THE INVENTION

Figure 1:
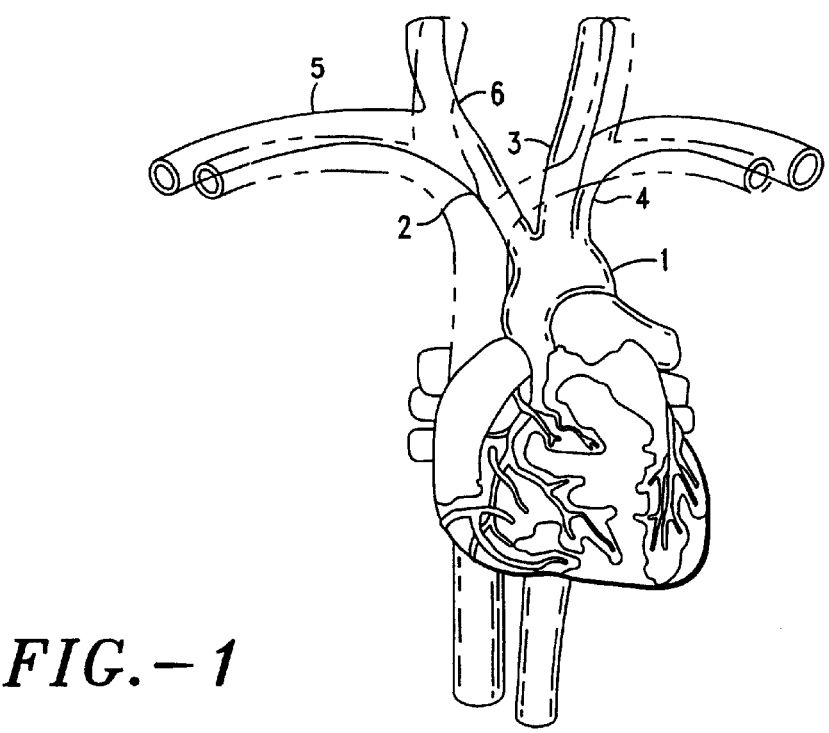
FIG. 1 is a diagram of the central cardiovascular system, showing the asymmetry of origins of the vessels off the aortic arch.

Functionally the heart is divided into two sides or sections. The right or pulmonary circulation section that receives blood from the veins of the body and pumps it through the lungs and the left or systemic circulation section that receives the blood from the lungs and pumps it to the body. Th blood is then collected in the veins to be returned to the right side of the heart. This anatomy is generally shown in FIG. 1. The arterial system begins at the aorta 1, to which the left ventricle of the heart pumps. The first three branches of the aorta are the brachiocephalic or innominate artery 2, the left (common) carotid artery 3, and the left subclavian artery 4. The brachiocephalic artery branches into the right subclavian 5 and right (common) 6 carotid arteries. These arteries provide the blood supply for the head and upper extremities. The aorta then passes down (caudad) through the body, continuing to provide arterial branches to organs, terminating as a bifurcation creating the iliac arteries. The brachiocephalic or innominate artery is the first branch of the aorta. It in turn branches into the right subclavian and right carotid arteries. In contrast, the left subclavian and left carotid arteries originate directly off the aortic arch. Thus, the subclavian and carotid arteries and any of their branches have different paths from their counterparts on the opposite side of the body.

Because of the different origins from the aorta and different branching pattern of the arterial tree, it can be appreciated that blood ejected from the left ventricle will not follow symmetrical pathways to opposite arms or opposite sides of the head. Similarly, the pressure pulse wave associated with left ventricular ejection will follow different pathways, and can be expected to arrive at different times for paired organs or members of the upper body.

Measurements performed by the inventor have shown this delay can range from less than one millisecond to several milliseconds, depending on the subject and circumstances. In addition, the inventor has found that this delay can be altered by several methods disclosed herein. This propagation delay, its alterations, and other factors make possible several determinations heretofore not possible by noninvasive means.

Blood pressure is the pressure exerted by the blood within a vessel upon the wall of the vessel. It is measured in units of force per unit area. Central venous pressure is the pressure within the large veins in the chest and the right atrium, which is the common emptying point for the venous system. Cardiac output is the amount of blood pumped by the heart, expressed in units of volume per time.

Central venous pressure (CVP) is defined as the distending pressure present in the veins in the chest (proximate to the heart), and is considered equal to the pressure in the right atrium (which is the emptying point for the venous system). Pressure should be the same throughout the venous system, but there are valves to ensure that the blood does flow back toward the heart (for example, when standing the venous blood must flow uphill, and there is no pump as on the arterial side).

As discussed in detail below, the present invention generally includes a radiation emitter having at least one wavelength being applied through a patient's tissue to the patient's blood; a radiation detector which detects reception of the at least one wavelength after absorbance through the blood, a movement generator for inducing position changes in the tissue; and a controller for computing the various characteristics based on the absorbance of the at least one wavelength of radiation at various position levels. In a preferred embodiment, the radiation emitter and detector are inserted in a probe which can be placed about the tissue/blood to be measured. A number of suitable configurations for probes are shown in FIGS. 2–8.

Figure 2:
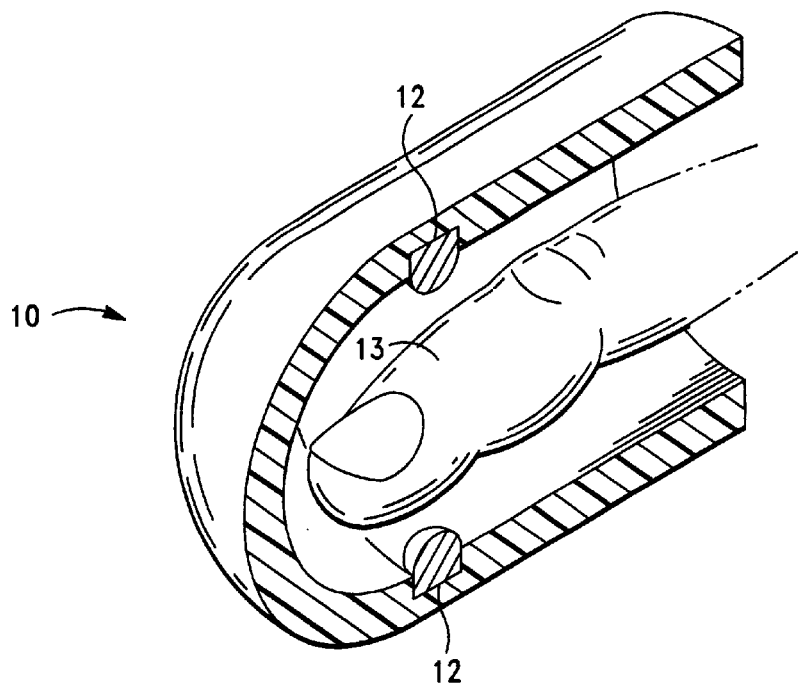
FIG. 2 shows a representative probe of the invention with a single emitter-detector pair.
Figure 3:
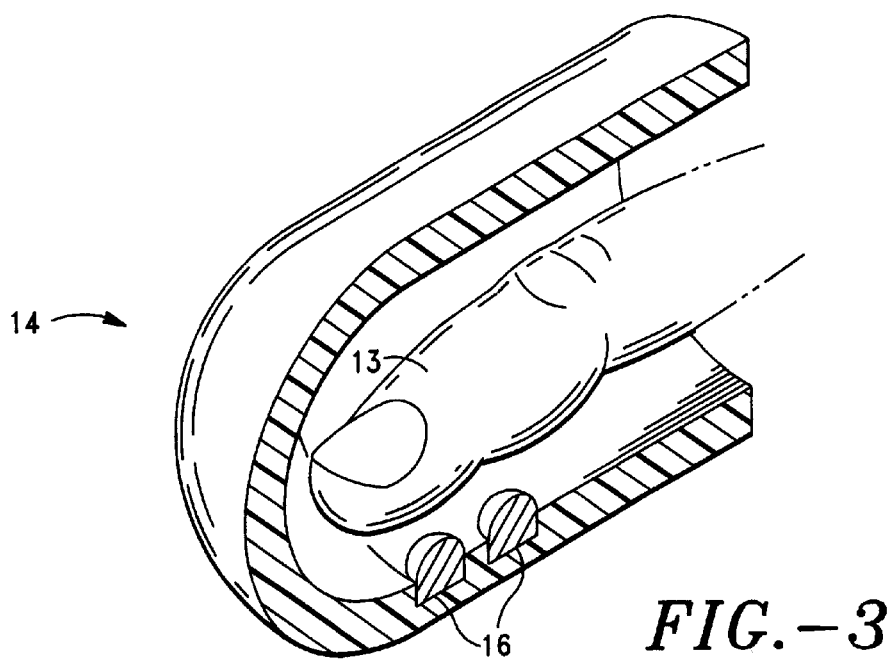
FIG. 3 shows an alternative embodiment of a probe of the invention with a single emitter-detector pair.
Figure 4:
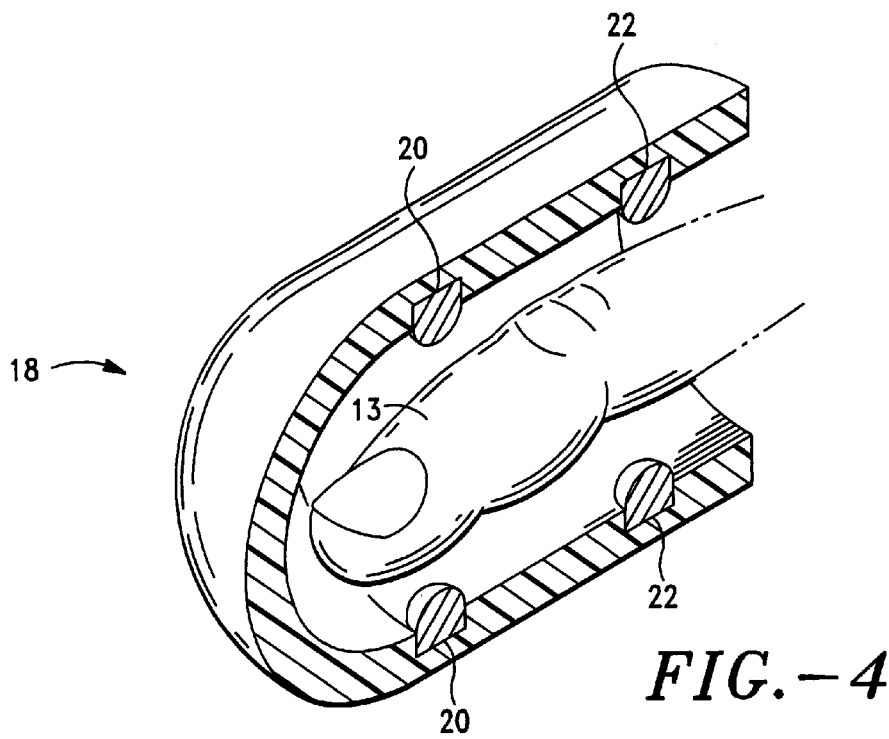
FIG. 4 shows a probe of the invention with two emitter-detector pairs spaced a known distance apart. This can be used to measure the velocity of the pulse wave within the probe itself.

For example, FIG. 2 shows a representative probe 10 with a single emitter-detector pair 12. The emitter and detector are placed such that transmittance through a body member, such as a finger 13, is measured. Generally, any part of the body that can be successfully transilluminated with the radiant energy used can be utilized. Thus, toes, ears, etc. could also be used. In addition, pulse oximetry can be accomplished with this and all of the following embodiments. FIG. 3 shows a representative probe 14 with a single emitter-detector pair 16 placed such that reflectance of a body member, such as a finger, is measured. Further, FIG. 4 shows a probe 18 with two emitter-detector pairs 20 and 22 spaced a known distance apart. This can be used to measure the velocity of the pulse wave within the probe itself.

Figure 5:
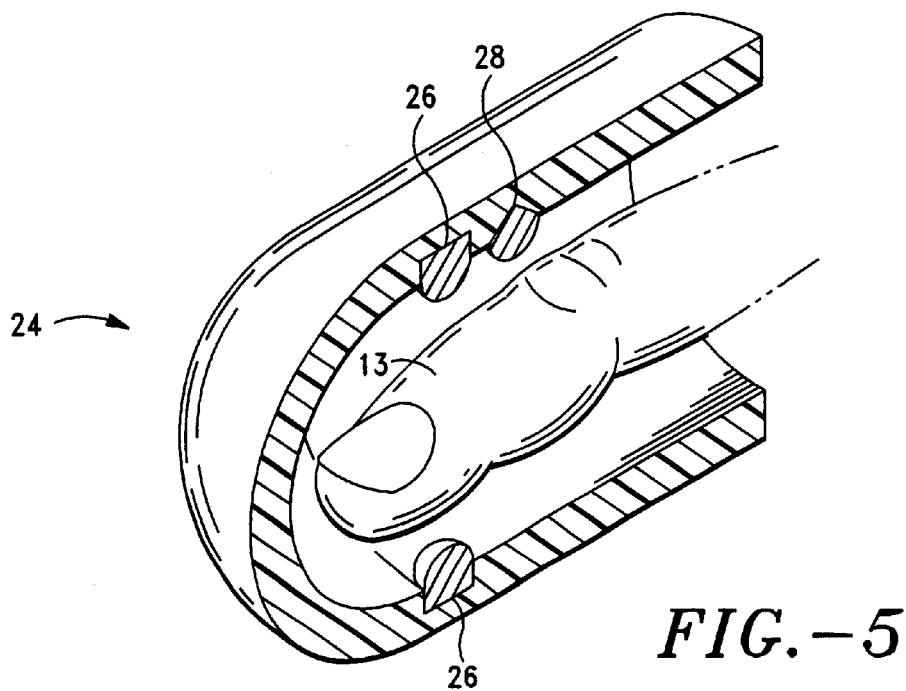
FIG. 5 shows a probe with a single emitter-detector pair and a single electrocardiogram (ECG) electrode.
Figure 6:
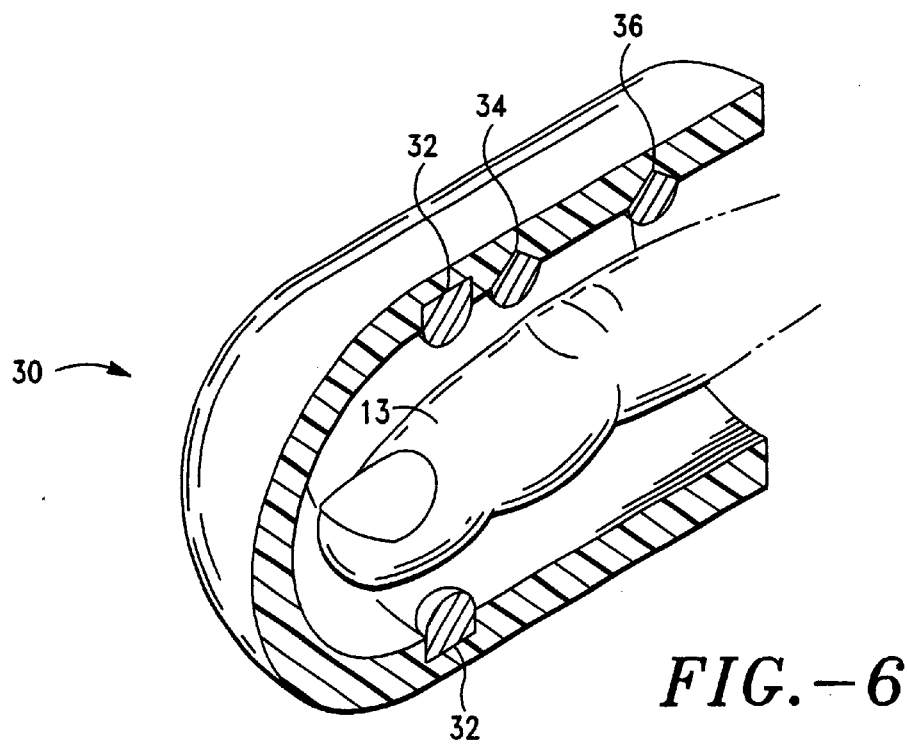
FIG. 6 shows a probe with a single emitter-detector pair and two ECG electrodes.
Figure 7:
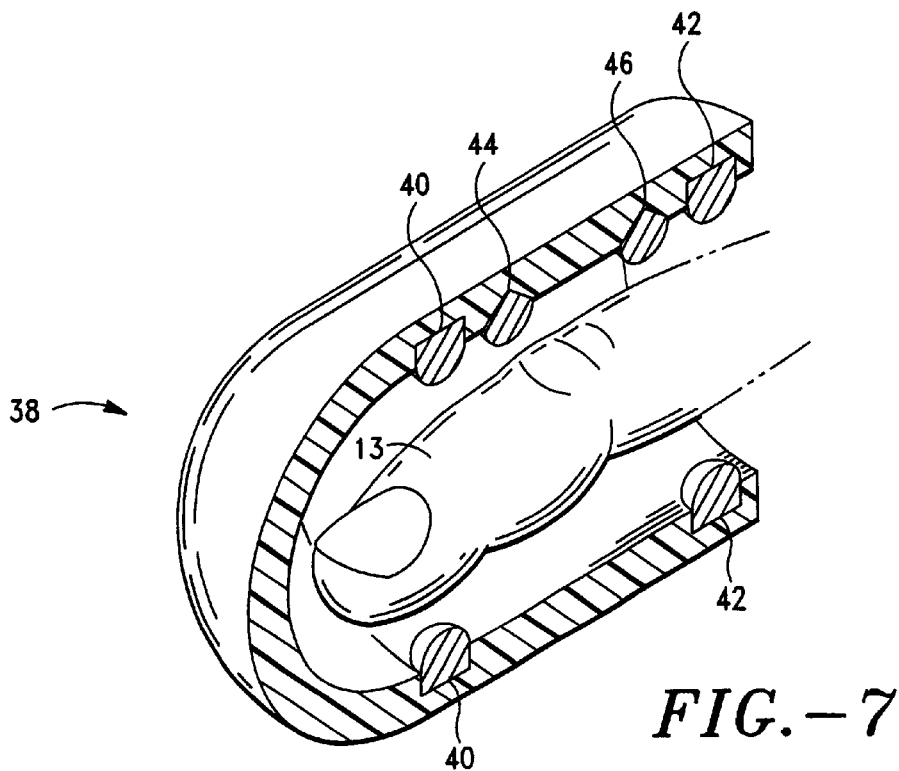
FIG. 7 shows a probe with a two emitter-detector pairs and two ECG electrodes.

In certain embodiments of the invention, the probe comprises one or more electrocardiogram (ECG) electrodes in conjunction with the emitter-detector pairs. For example, FIG. 5 shows a probe 24 with a single emitter-detector pair 26 and a single electrocardiogram (ECG) electrode 28. Similarly, FIG. 6 shows a probe 30 with a single emitter-detector pair 32 and two ECG electrodes 34 and 36 and FIG. 7 shows a probe 38 with a two emitter-detector pairs 40 and 42 and two ECG electrodes 44 and 46. Such probes, if placed on opposite extremities of a patient, can be used to measure central and peripheral pulse wave velocity as well as ECG. Other configurations, such as double emitter-detector pairs and single ECG electrode, can be envisioned.

Figure 8:
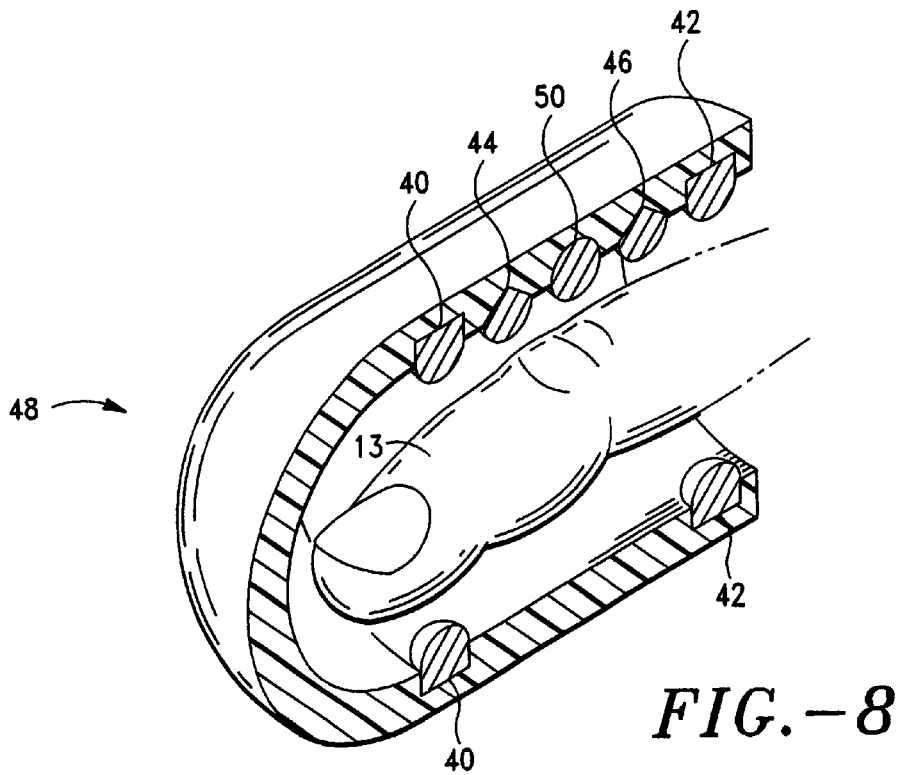
FIG. 8 shows a probe of the invention further comprising a position sensor.

In yet other embodiments of the invention, the probe further comprises a position sensing or measuring device together with the emitter-detector pairs and/or ECG electrodes. FIG. 8 shows a probe 48 similar to that shown in FIG. 7 with the addition of a position sensor 50. This position sensor could be used in conjunction with a position sensor placed at heart level in order to determine the hydrostatic pressure difference between the two position sensors.

As discussed in detail herein, the invention employs hydrostatic pressure to enable precise self-callibration of the devices in a completely non-invasive manner. Hydrostatic pressure affects all liquids. Gravity or other acceleration will affect both the arterial and venous sides of the circulation. It affects all aspects of the blood pressure equally—mean, systolic, diastolic. For example, an increase in height which causes a change of 10 torr will change every pressure measurement during the cardiac cycle by this amount.

For example, if the "true" blood pressure (taken level with the heart) is 120/80, when the arm is raised an amount needed to decrease the measured pressure by 10 torr, the measured pressure in the arm will be 110/70. The pulse pressure will be the same, but the transmural pressure will be 10 torr lower at all times. In addition, the vessel will be smaller at all points.

The heart is taken to be the center of the circulatory system, and all values are in reference to it. This is not necessary for the practice of the invention, but serves as reference points for values in the current medical literature.

The electromagnetic radiation in this description will refer to light in the visible and infrared range although, as noted in the attached claims, it is conceivable that other forms could be used.

Similarly, while the present invention primarily describes the use of transillumination, it will be appreciated that reflectance spectrophotometry may alternatively be employed.

Operating Principles

It is well known that Incident radiation passing through a body part is attenuated (absorbed) in the tissue. The theoretical basis for spectrophotometic techniques is Beer's law (the Beer-Lambert-Bouguer law) which expresses the incident intensity in terms of transmitted intensity and extinction coefficients of the tissue compartments through which the radiation has passed. The equation can be written as:

$$ln(I/Io) = E*C*L \qquad \text{Eq.1}$$

Where:
  Io=the incident intensity of the source radiation;
  I=the transmitted intensity of the source through the sample;
  E=the extinction coefficient of the component of interest;
  C=the concentration of the component in the tissue itself;
  L=the optical path length (distance) through the absorber; and
  E*C*L=absorbance.

Beer's law and the practice of spectrophotometry and oximetry have been exhaustively reviewed in the literature. Generally, pulse oximetry in effect filters out signals other that pulsating (AC). In the body, it can be assumed that the pulsatile component of the signal is arterial blood, while all other tissue absorbers should be non-pulsatile (DC).

An additional feature of this invention, not found in any previous disclosure, is the use of hydrostatic pressure changes to vary the amount of venous blood within a body member such as a finger. Thus, hydrostatic changes can be used in a similar manner to the pulse to perform measurements on both arterial and venous blood. If a finger is contained within a probe, raising the probe will lower the hydrostatic pressure of all vessels in the finger, both arterial and venous. Both arteries and veins (and arterioles and venules) will be smaller due to lower pressure distending their walls. Most change will occur on the venous side of the circulation due to lower pressure. Total absorbance of the finger will decrease. As the arterial oxygen saturation can be measured by pulse oximetry, the venous oxygen saturation can be calculated in a similar manner.

A light signal of a known intensity and wavelength is produced by means of light-emitting diodes (LEDs) as in currently used oximeters or, as in one possible embodiment, a broad-band light source whereby wavelengths are isolated by a rotating filter or diffusion grating. In the latter case, the emitted light is distilled through a filter which allows a known wavelength and intensity of light to penetrate. Use of tunable lasers or other equipment is also possible. If the light source is proximate to the point of use, no further mode of transmission will be needed. If it is not, the light will be transported to the desired point by means such as a fiber optic cable, preserving the wavelength and intensity.

Several means of motion induction are possible. Various means of position measurement are also possible. For example, a liquid filled tube with an end open to the atmosphere can be employed. Other position sensors are known to those having skill in the art, and include electromagnetic, spectroscopic, and chemical means. A broad-band photo detector (in the case of visible or infrared light) or other means will be utilized to measure the quantity of transmitted light.

To generate a single data point, the movement induction means is used to bring the finger (or other space of interest) to a known position relative to the heart. Light of known wavelength and intensity is emitted (and transmitted if necessary) on the surface of interest. Detection of the light signal at a distinct point (normally opposing surface) is made and the relative absorbance and extinction of the signal is calculated. Signal processing is used to determine the pulsatile portion of the signal. The arrival time of the pulse is recorded, as is the amplitude and waveform. This measurement may be repeated one or more times to ensure the accuracy of the measurement; this can be done within a very short time frame (less than a millisecond).

To generate multiple data points, the process outlined in the previous step will be repeated at the next chosen wavelength, while still at the same predetermined position. The range and number of wavelengths can be selected, and changed for different applications.

Once the desired number of wavelengths has been examined, the movement induction means would bring the finger or other volume to a predetermined second position, and the data collection of steps would be repeated. At the completion of measurements and determinations for this second position, the movement induction means will bring the space to a third predetermined position, and the measurements and determinations repeated. This process would be continued until the desired range of positions has been scrutinized.

In order to make computations of pulse propagation delay, identical measurements would be made simultaneously with a probe on the same member on the opposite side of the body. For example, if one probe were placed on the index finger of the right hand, the other probe would be placed on the index finger of the left hand.

Because the arterial path to the arm is essentially identical after the second part of the subclavian artery, any differences in pulse wave velocity and pulse wave propagation time must occur prior to this point; that is, very close to the root of the aorta. In any case, pulse wave velocity increases rapidly as the pulse wave propagates down the aorta and into the periphery (Fung). Thus, any timing differences in the periphery will be greatly reduced by the high wave velocity, leaving central effects as the most prominent.

The apparatus of the invention can be operated intermittently or continuously. In the intermittent mode, a single set of calculations can be used for analysis to produce the determinations claimed. However, the device can also be easily operated in continuous mode, with the process outlined above repeated as often as wished (constantly if desired). In addition, a rapid ("stat") mode can be offered with the minimum number of measurements made that will provide an accurate estimation of correct values. Such a rapid mode would be useful in emergency situations.

While this methodology should give precise values, further adjustment may be desired to compensate for any discrepancies between theoretical and in vivo measurements. Contemporary oximeters in fact use a calibration curve when determining oxygen saturation, with the curve being generated with data from normal volunteers.

Calculations and Analysis

The following algorithms are further examples of the use of the present invention. Some variables have degrees of co-dependence. In these cases, values are calculated by iterative computational techniques.

Figure 9:
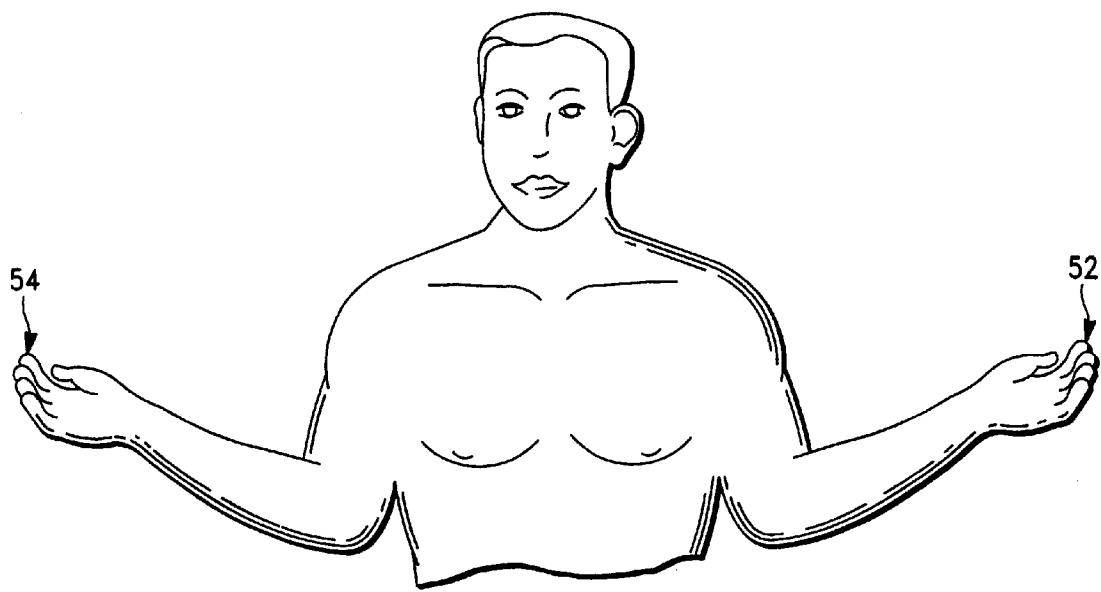
FIG. 9 shows an embodiment of the invention with probes placed on opposite digits of a subject.
Figure 10:
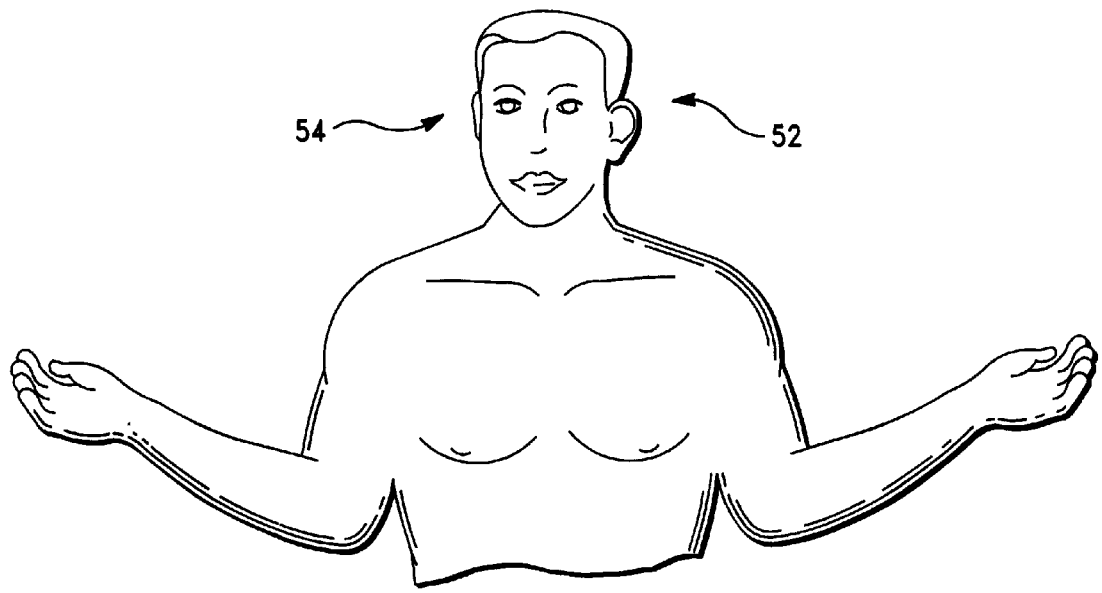
FIG. 10 shows an embodiment of the invention with probes placed on opposite temples of a subject.

Generally, measurement of pulse wave amplitude and timing is made using probes such as that shown in FIG. 2, using methods similar to standard oximetry described in the prior art. As shown in FIG. 9, a first probe 52 is placed on a finger and set at a known position relative to the heart. Another, simultaneous measurement of pulse wave amplitude and timing is made by a second probe 54 placed on a finger on the hand opposite that of the first probe. The pulse delay occurring between the two measurements is made. Alternatively, as shown in FIG. 10, probes 52 and 54 can be placed on opposite temples of the patient to measure pulse wave values and delay. The probes can also be placed on the patient's ears.

From this information alone, an estimate of pulse wave velocity at the aortic root could be made, by utilizing a table of normal values for the distance of the central anatomical difference.

If a measurement of blood pressure is then made, one can perform the following calculation:

$$p = c^* u^* \rho \qquad \text{Eq. 2}$$

Where:
c=pulse wave velocity;
u=flow wave velocity; and
$\rho$=the density of the blood (approximately 1.055 grams/cm$^3$).

According to the invention, p and c have been measured, $\rho$ is known. This allows one to solve for u, which is the flow wave velocity at the aortic root. This by itself is a measure of cardiac output. If one makes an estimate of aortic root diameter, one can then compute cardiac stroke volume.

Techniques described by O'Rourke and others describe reconstruction techniques that can be used to convert or "transform" peripheral blood pressures and waveforms to the corresponding pressure and waveform at the aortic root. Ideally, the blood pressure at the aortic root should be used as the pressure term in Fung's equation.

One can improve on the above determination in several ways. The first way is by additionally measuring the peripheral pulse wave velocity. To do this, measurement of pulse wave amplitude and timing is made by a first probe such as that shown in FIG. 5. The probe is at a set known position relative to the heart. Another, simultaneous measurement of pulse wave amplitude and timing is made by a second probe placed on a finger on the hand opposite that of the first probe. The pulse delay occurring between the two measurements is made. The respective peripheral pulse wave velocities are also computed. If the peripheral pulse wave velocities are different, it can be assumed that this is because of the different central anatomies from which the respective pulses traveled. This information alone may be enough to compute central pulse wave velocity from a table of normals. However, when combined with the pulse wave delay information, this data enables one to construct a function of pulse wave speed from the periphery back to the aortic root, thus giving another measure of central pulse wave velocity.

Another method of the invention is to vary the position of the probes relative to the heart. If the first probe is at heart level and the second probe is raised above (with respect to the earth) heart level, the hydrostatic pressure of the blood vessels within the second probe will be lower than those within the first probe. In turn, in accordance with Fung's equation stated above, this means that the pulse wave velocity of the arterial vessels within the second probe will be lower than that in the arterial vessels within the first probe. This will change both the measured pulse delay between the two probes, and the measured peripheral pulse wave velocities. This creates additional measurements by which to compute central pulse wave velocity.

According to the invention, changes in hydrostatic pressure are controlled by the following equation:

$$p = \rho^* g^* h \qquad \text{Eq. 3}$$

Where:
$\rho$=blood density;
g=gravitational acceleration; and
h=height above a reference point (with respect to the earth).

The difference in hydrostatic pressure between the vessels in two probes is thus governed completely by their difference in heights relative to the heart (referenced to the surface of the earth). Therefore, a known change in position produces a known change in hydrostatic pressure.

According to the invention, the above measurements can be employed to derive a number of physiological properties. Preferably, the probes of the invention are connected to a controller to aid the data collection and analysis used to make the desired determination. The controller includes a computing device or standard personal computer (PC) with a monitor. Included within the controller are algorithms for the calculation of variables not measured directly.

Figure 11:
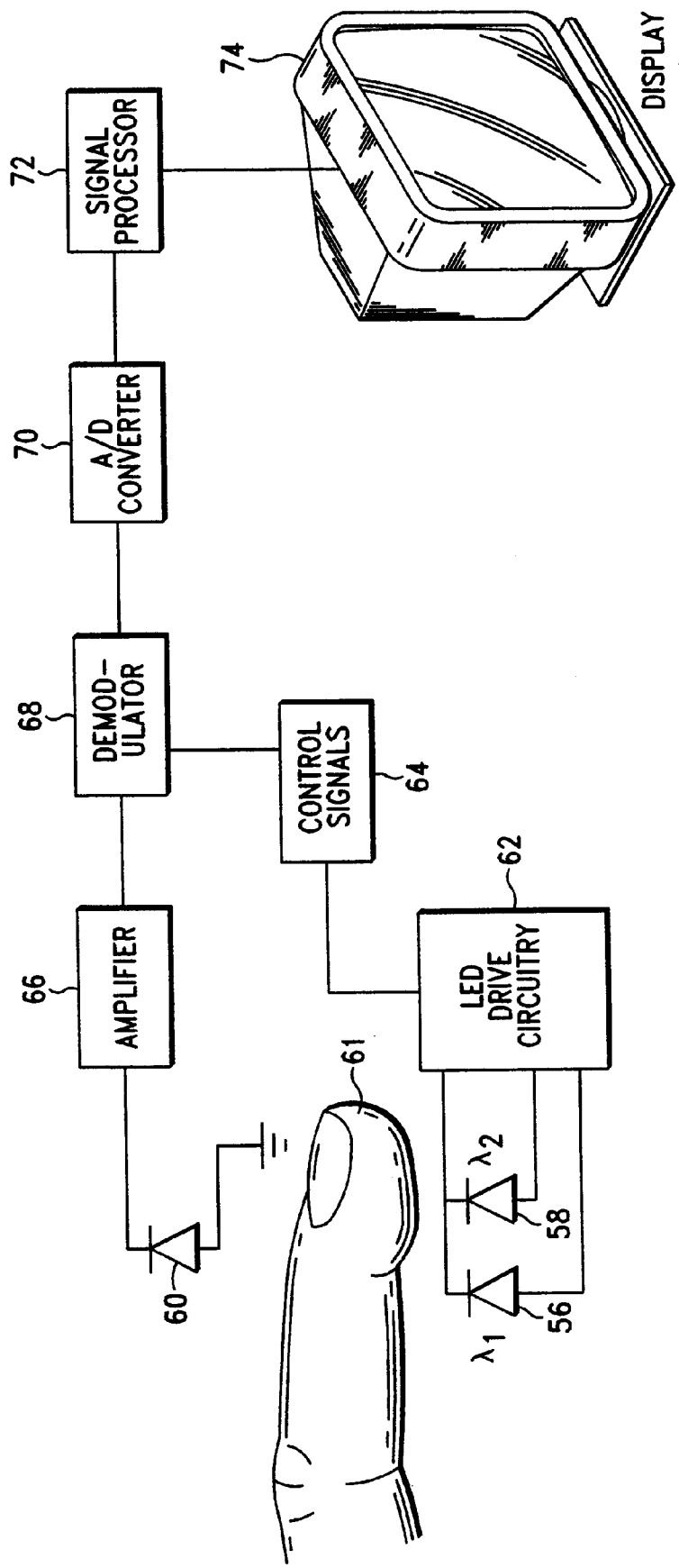
FIG. 11 shows a circuit schematic of the invention comprising a photoplethysmogram.

For example, FIG. 11 shows a circuit schematic for a one or two wavelength photo-plethysmograph. Emitters 56 and 58 and detector 60 are positioned adjacent the tissue being measured, such as a finger 61. Emitters 56 and 58 are driven by drive circuitry 62, which is in turn governed by control signal circuitry 64. Detector 60 is connected to amplifier 66. The signal from amplifier 66 is sent to demodulator 68, which is also synched to control signal circuitry 62. The signal from the demodulator 68 is sent to analog-digital converter 70. The desired computations are performed on the output from the converter 70 by signal processor 72 and the results sent to display 74. Emitters 56 and 58 operate specific wavelengths, such as 805 nm, and may comprise light emitting diodes (LEDs) or laser diodes. Detector 60 preferably comprises a silicon photodiode. Such emitter-detector pairs are shown in FIGS. 2 and 3.

Figure 12:
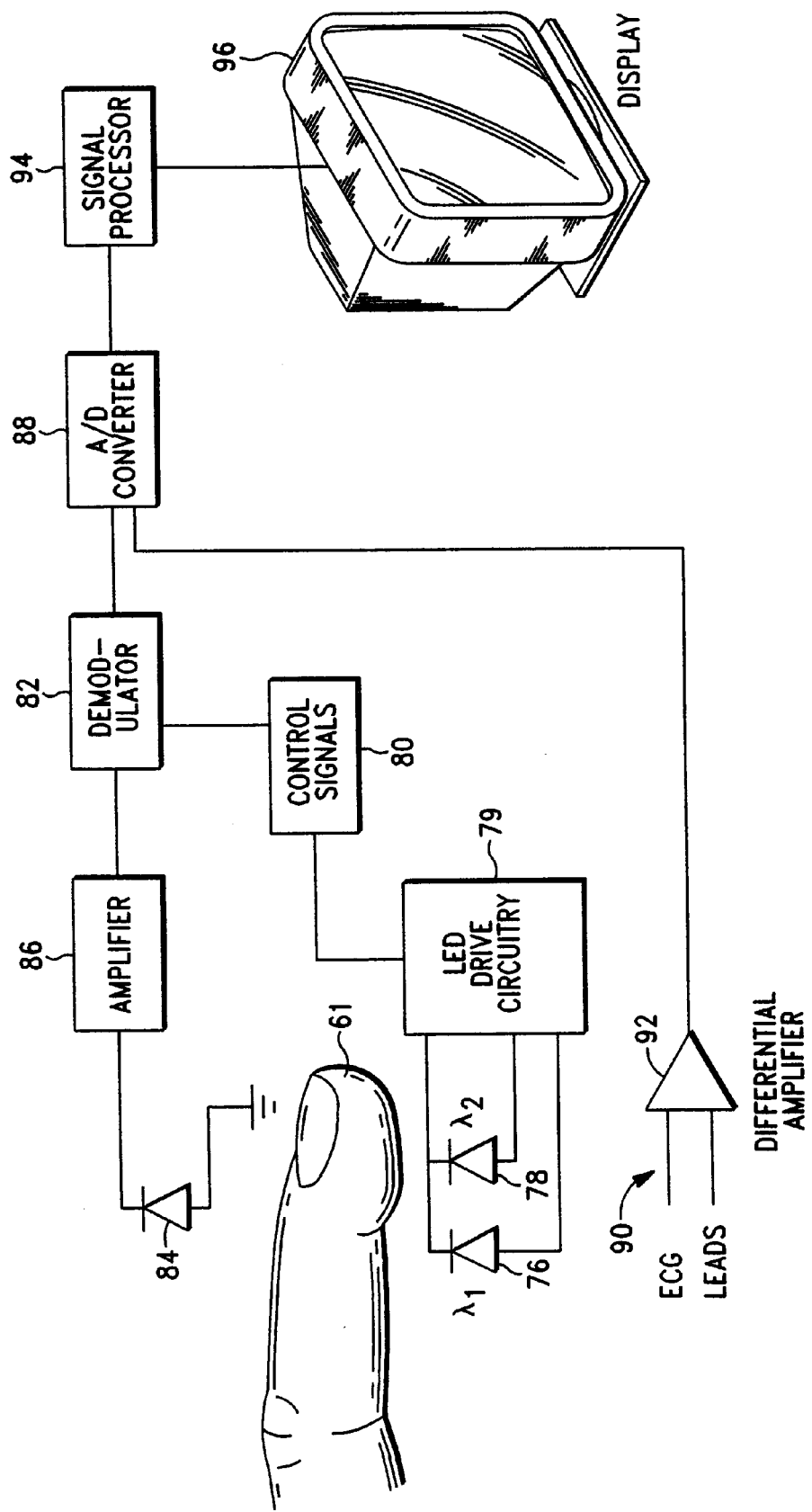
FIG. 12 shows a circuit schematic of the invention comprising a photoplethysmogram with an ECG amplifier.

FIG. 12 shows a schematic of an alternate embodiment of suitable circuitry. As with FIG. 10, emitters 76 and 78 are connected via LED drive circuitry 79 and control signal circuitry 80 to demodulator 82. Signal from detector 84 is amplified at circuit block 86 and sent to demodulator 82. Output from demodulator 82 is sent to A/D converter 88. In addition, ECG leads 90 are connected to differential amplifier 92 and the signal is sent to converter 88. Output from converter 88 is processed at block 94 and the results sent to display 96. A probe such as those shown in FIGS. 5 and 6 may be used with the circuitry. The ECG leads are preferably silver/silver chloride or stainless steel.

Figure 13:
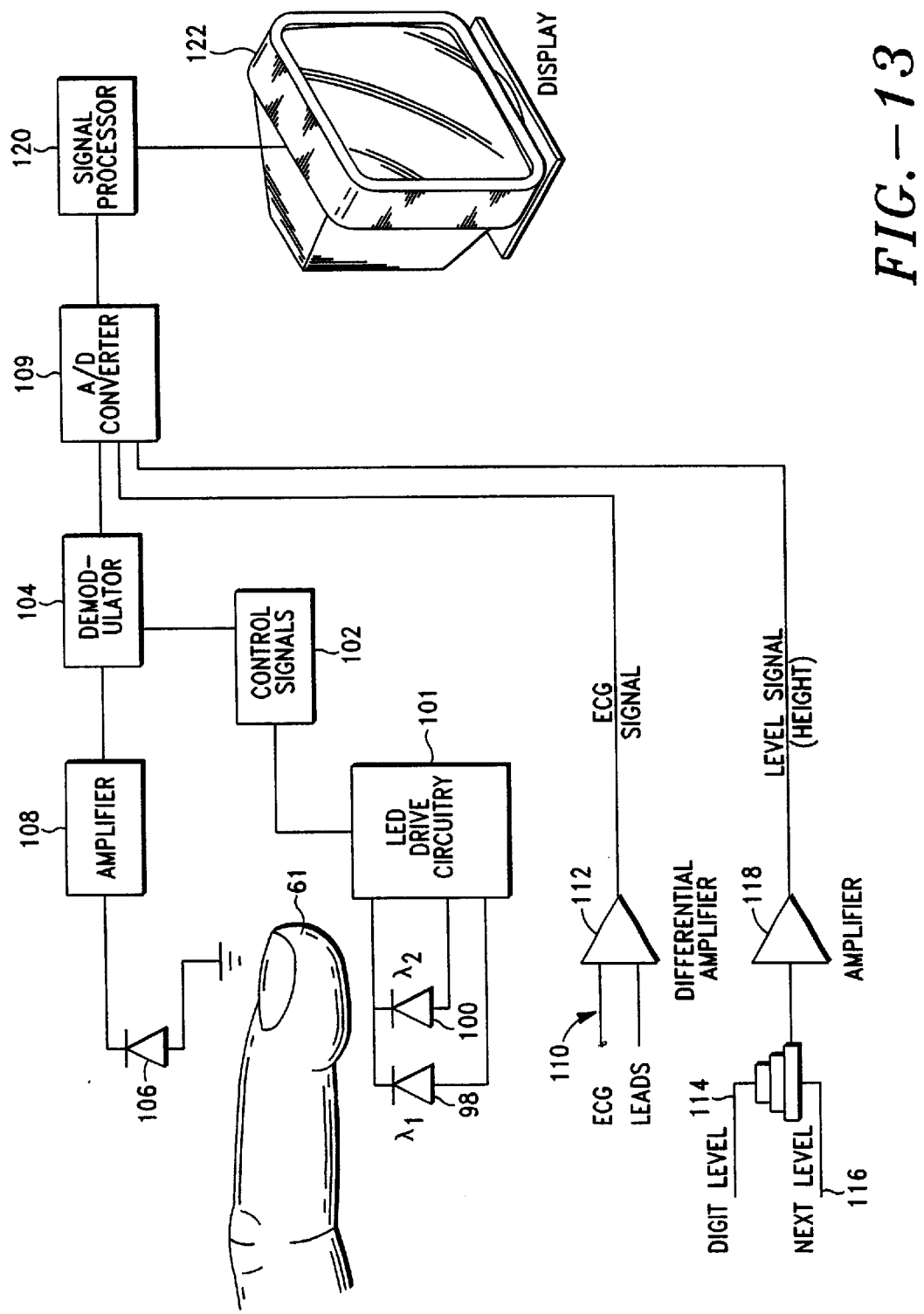
FIG. 13 shows a circuit schematic of the invention comprising a photoplethysmogram with an ECG amplifier and a level signal.

Yet another embodiment of the invention is shown in FIG. 13. Emitters 98 and 100 are connected via LED drive circuitry 101 and control signal circuitry 102 to demodulator 104. Signal from detector 106 is amplified at circuit block 108 and sent to demodulator 104. Output from demodulator 104 is sent to A/D converter 109. ECG leads 110 are connected to differential amplifier 112 and the signal is sent to converter 109. Digit level sensor 114 and heart level sensor 116 are connected to amplifier 118 and the signal is sent to converter 109. Output from converter 109 is processed at block 120 and the results sent to display 122.

Figure 14:
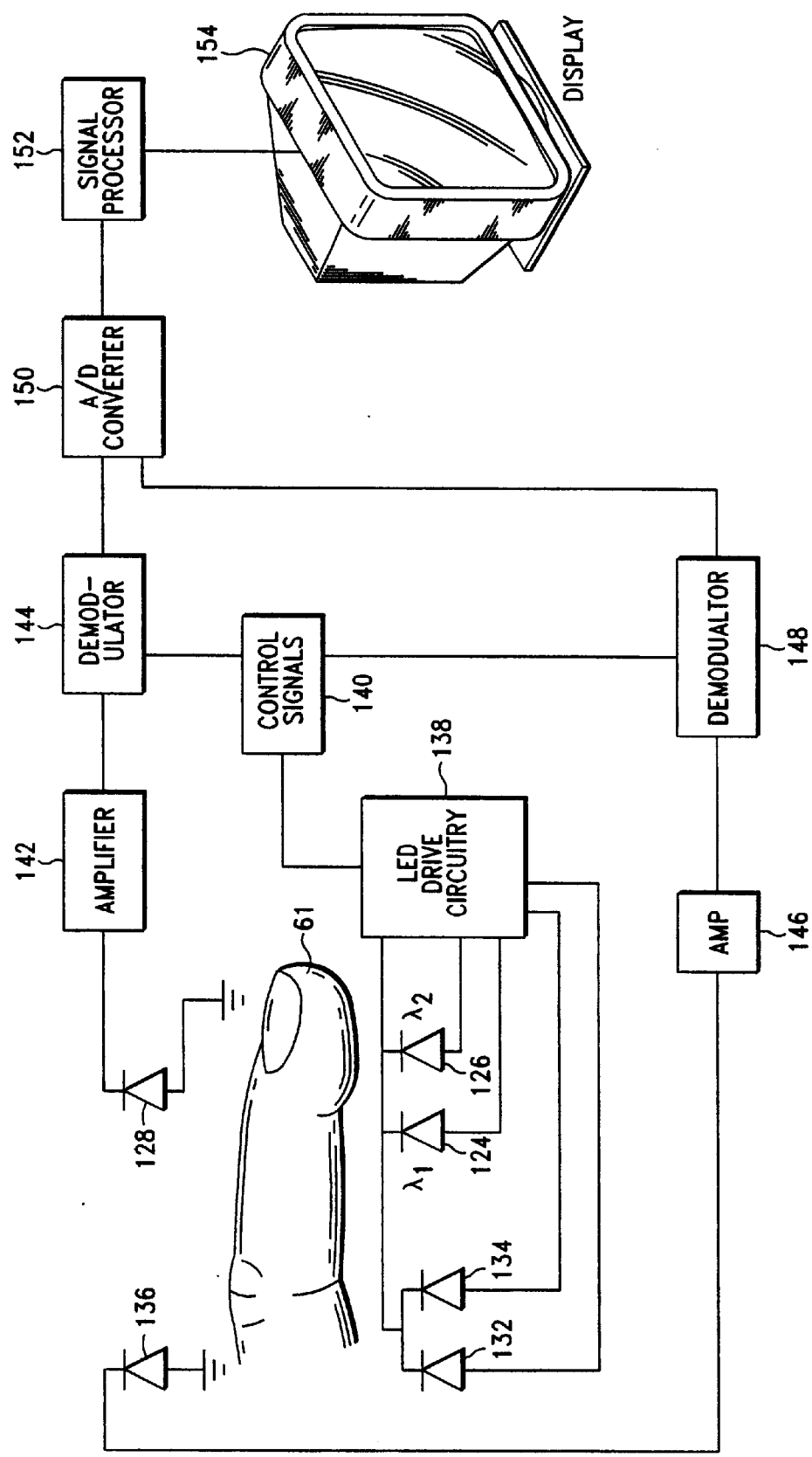
FIG. 14 shows a circuit schematic of the invention comprising a photoplethysmogram with two independent channels.

FIG. 14 shows a circuit schematic suitable for use with a probe having two physically independent channels, such as the one shown in FIG. 4. A first emitter-detector pair comprising emitters 124 and 126 and detector 128 are positioned adjacent the tissue being measured, such as a finger. A second pair comprising emitters 132 and 134 and detector 136 are positioned a selected distance from the first pair. Emitters 124, 126, 132 and 134 are driven by drive circuitry 138, which is in turn governed by control signal circuitry 140. Signal from detector 128 is amplified by block 142 and sent to demodulator 144. Independently, signal from detector 136 is amplified and demodulated at blocks 146 and 148, respectively. Output from demodulators 144 and 148 is sent to analog-digital converter 150. The desired computations are performed on the output from the converter 150 by signal processor 152 and the results sent to display 154.

Figure 15:
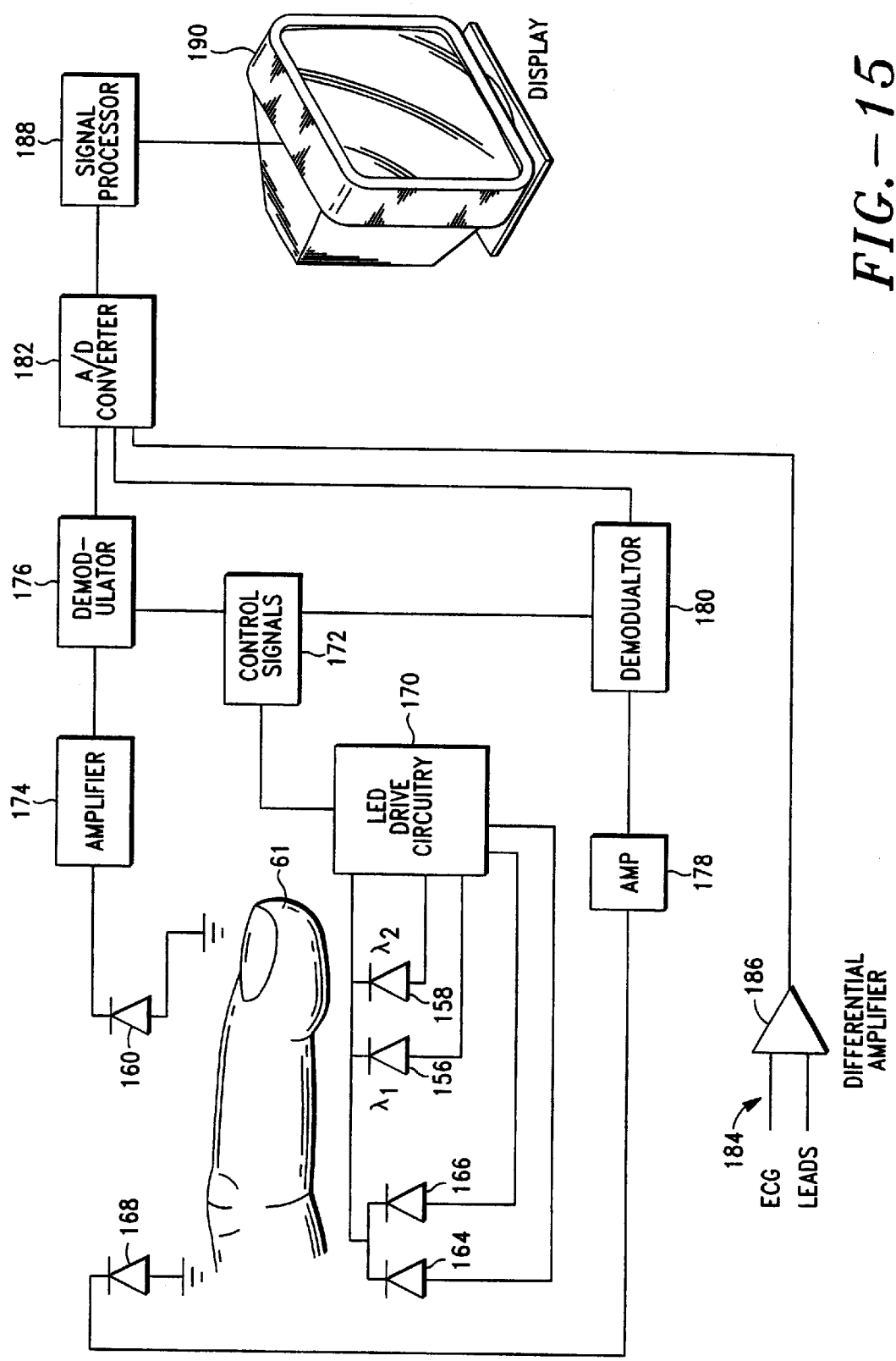
FIG. 15 shows a circuit schematic of the invention comprising a photoplethysmogram with two independent channels and an ECG amplifier.

An alternative embodiment configured for use with a probe having two physically independent channels and an ECG lead, such as the one shown in FIG. 7, is schematically shown in FIG. 15. A first emitter-detector pair comprising emitters 156 and 158 and detector 160 are positioned adjacent the tissue being measured, such as a finger. A second pair comprising emitters 164 and 166 and detector 168 are positioned a selected distance from the first pair. Emitters 156, 158, 164 and 166 are driven by drive circuitry 170 which is in turn governed by control signal circuitry 172. Signal from detector 160 is amplified by block 174 and sent to demodulator 176. Independently, signal from detector 168 is amplified and demodulated at blocks 178 and 180, respectively. Output from demodulators 176 and 180 is sent to analog-digital converter 182. ECG leads 184 are connected to differential amplifier 186 and the signal is also sent to converter 182 The desired computations are performed on the output from the converter 182 by signal processor 188 and the results sent to display 190.

Figure 16:
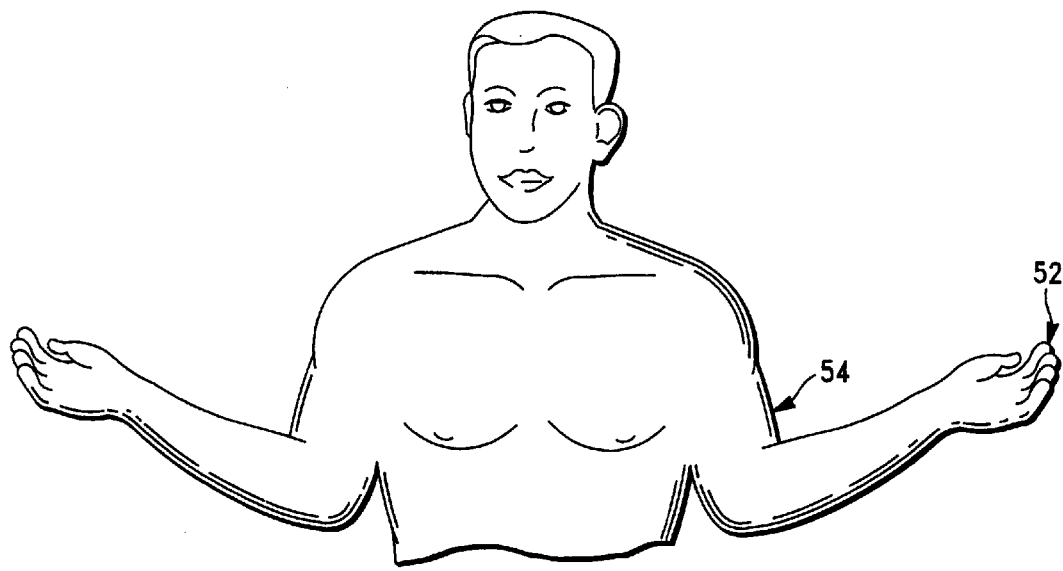
FIG. 16 shows an embodiment of the invention with probes placed on the digit and on the arm near the brachial artery.
Figure 19:
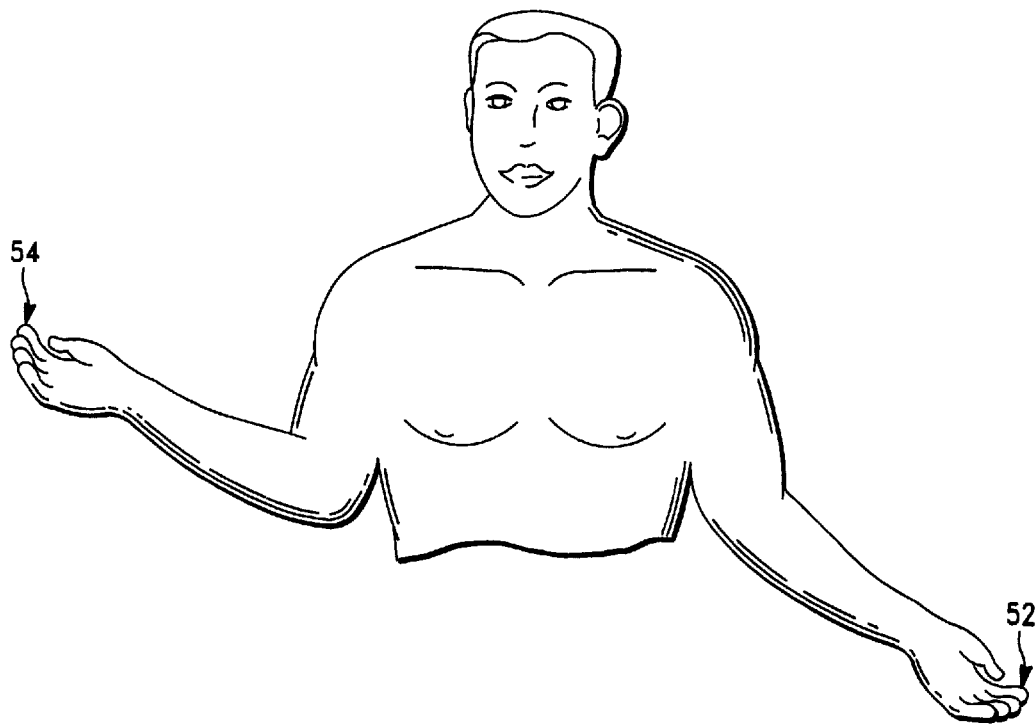
FIGS. 19 and 20 show embodiments of the invention with probes placed on opposite digits of a subject positioned at differential heights relative to the patient's heart.
Figure 17:
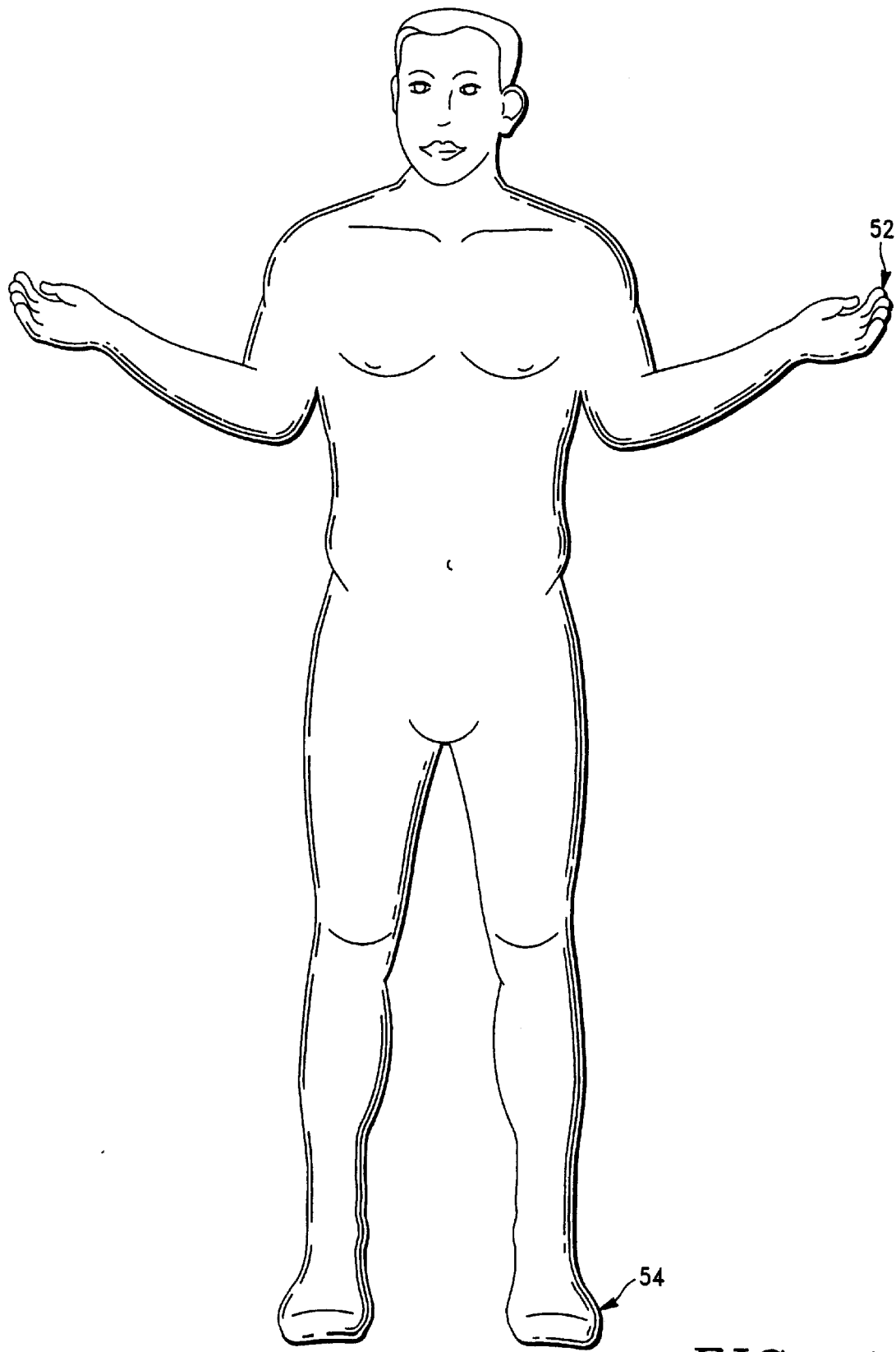
FIG. 17 shows an embodiment of the invention with probes placed on a finger and on a toe.
Figure 20:
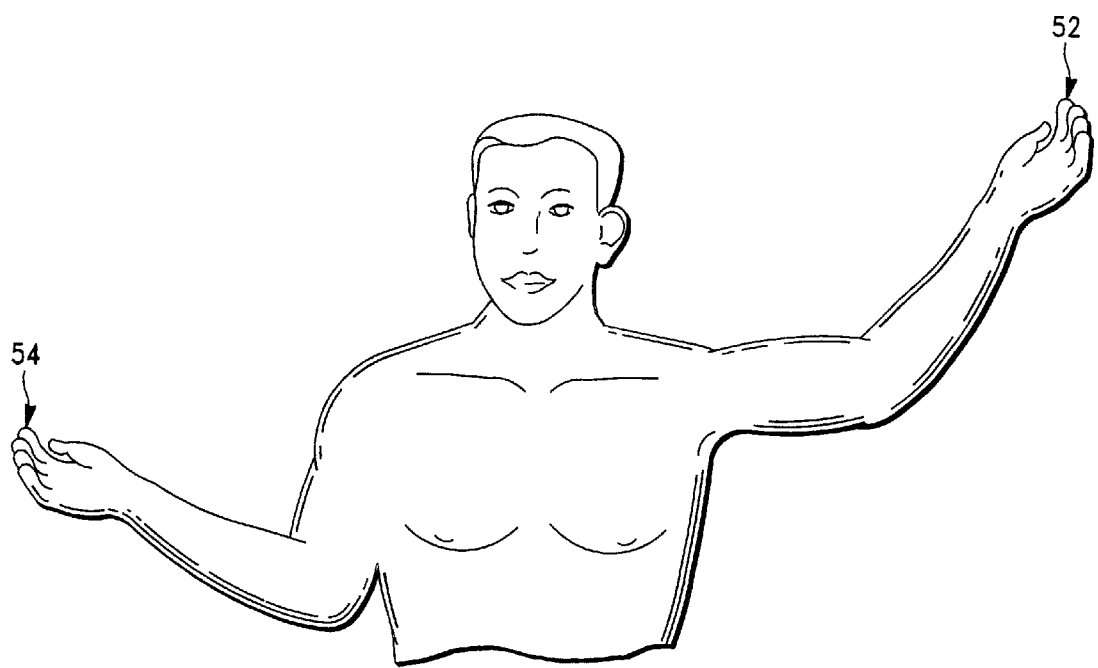
Figure 21:
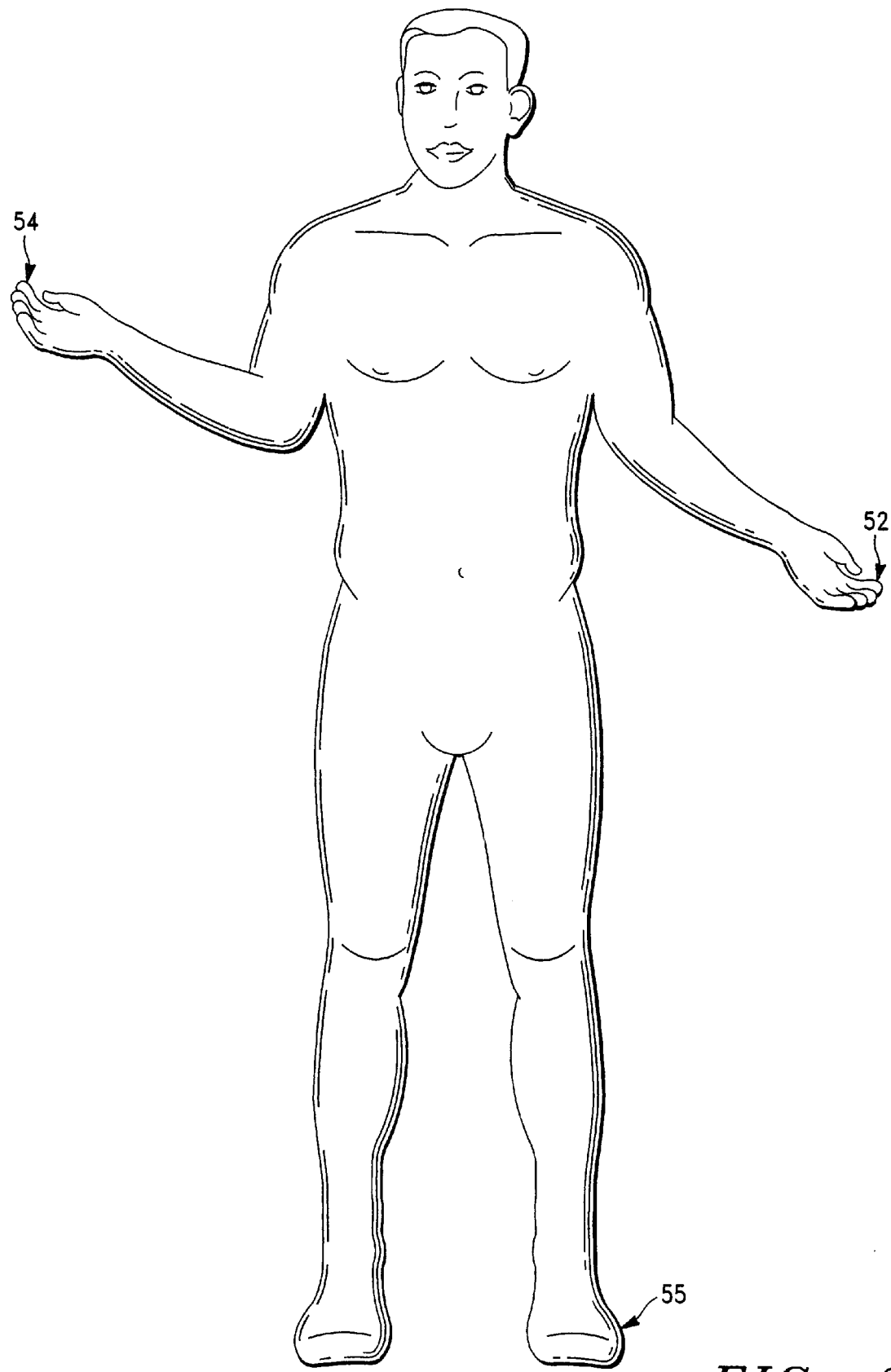
FIG. 21 shows an embodiment of the invention with probes placed on opposite fingers positioned at differential heights and on a toe.

As one of ordinary skill in the art will appreciate, the placement of the various probes discussed above will effect the types of measurements that can be taken. As discussed above, FIGS. 9 and 10 show probes placed on opposite extremities to enable measurement of pulse wave delay. FIG. 16 shows an embodiment of the invention with probe 52, such as in FIG. 1, placed on the digit, and a probe 54, such as in FIG. 2, placed on the arm near the brachial artery. This could measure the pulse wave velocity in the arm (as well as pulse oximetry). A similar embodiment could measure pulse wave velocity in the leg. FIG. 17 shows probes 52 and 54 placed on a finger and on a toe to measure the pulse wave delay. FIG. 18 shows probes 52 and 54 placed on opposite digits and probe 55 placed on a toe. This allows measurement of the differential pulse wave delay between the fingers and toe, and allows calibration of the toe probe to be used in place of a finger probe (if only one finger probe could be used, such as in hand surgery). The use of appropriate probes also allows a diagnostic-quality ECG. FIGS. 19 and 20 show probes 52 and 54 placed on opposite digits. One arm of the subject is placed at the level of the heart, while one arm is moved to different positions, both above and below the level of the heart. By generating different hydrostatic pressures in the vessels, the pulse velocity and hence pulse wave delay changes. In addition, the amplitude of the pulse wave, and amplitude of venous absorbance changes. This allows the additional computations of arterial blood pressure and venous pressure. FIG. 21 shows probes 52 and 54 placed on opposite digits and probe 55 placed on a toe. The differential hydrostatic pressures in the vessels allow measurements of pulse wave velocity and pulse wave delay, as well as arterial blood pressure and venous pressure. Use of probes with suitable ECG leads will also allow the invention to perform a diagnostic-quality ECG. In addition, heart rate and respiratory rate can be calculated, and cardiac output and several other cardiovascular characteristics computed.

Figure 22:
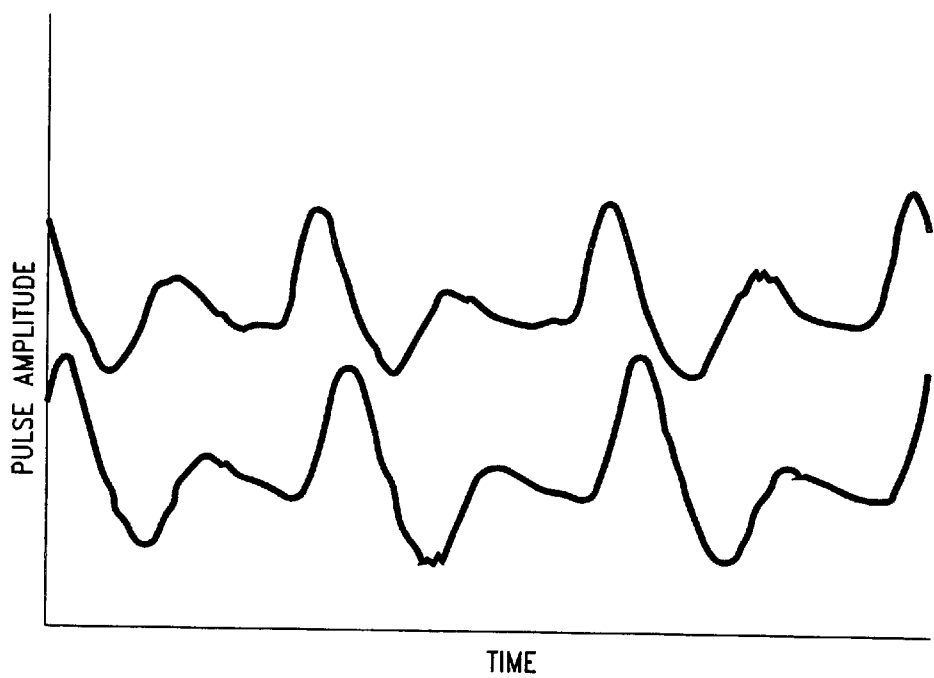
FIGS. 22–25 are graphical representations of an oscilloscope screen showing recordings using methods of the invention.
Figure 23:
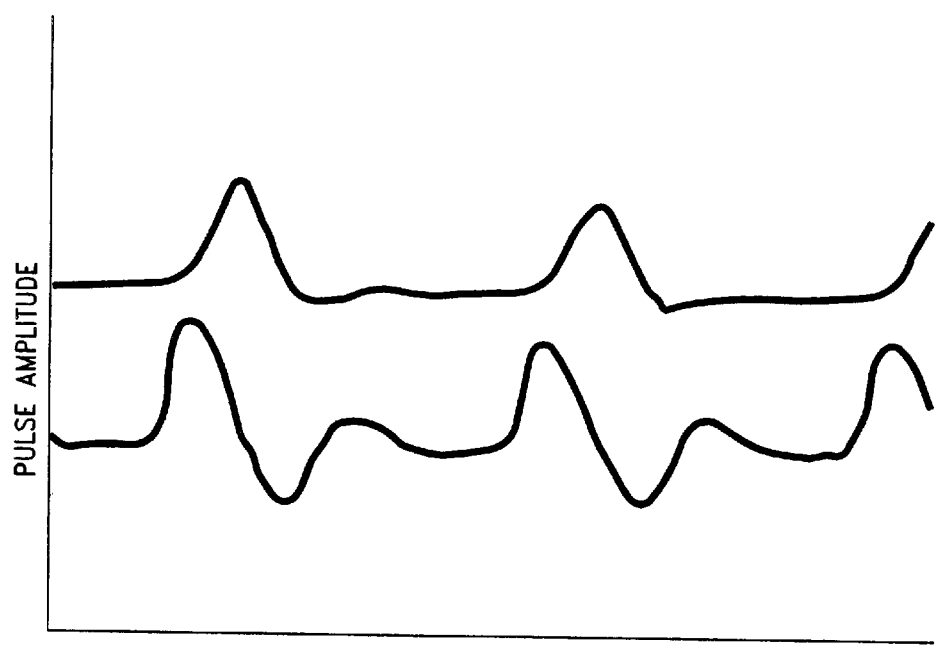
Figure 24:
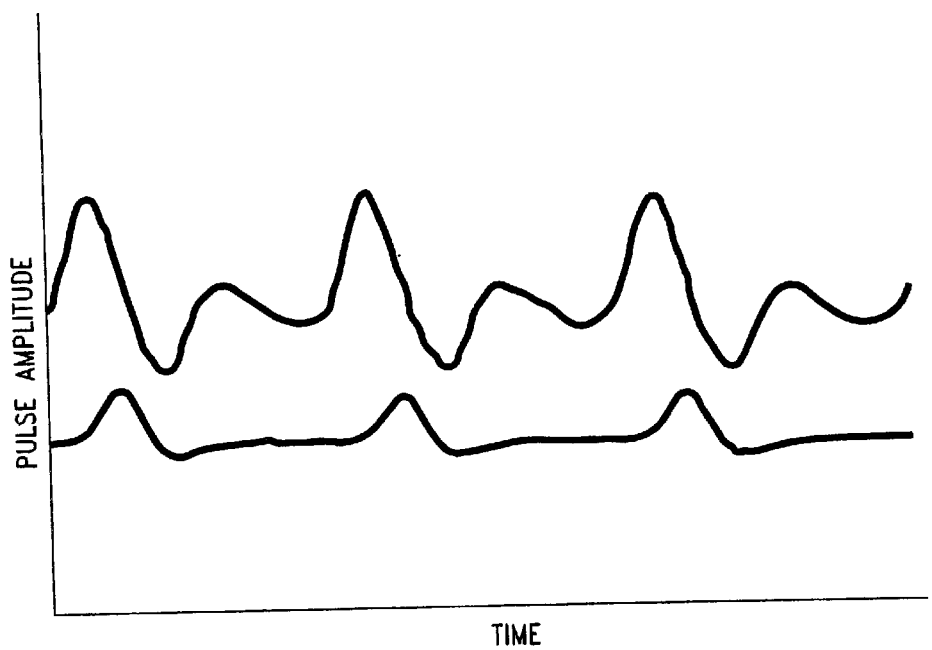
Figure 25:
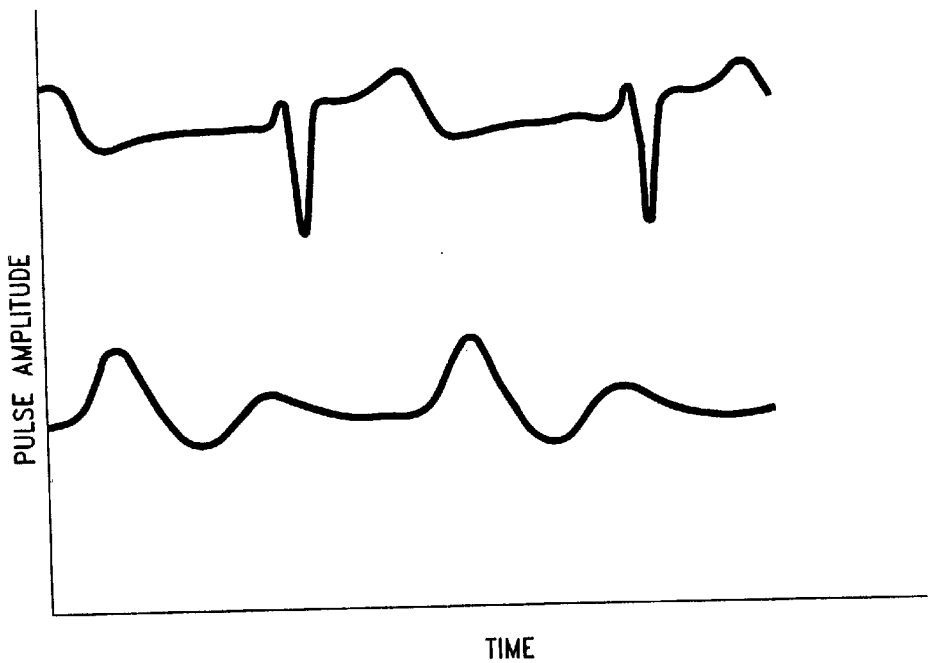

As discussed above, the controllers of the invention preferably output the results of the measurements and computations to a display. FIG. 22 shows an oscilloscope screen. The two tracings are from pulse oximeter probes, such as those shown in FIG. 1, placed on the index fingers of both hands. The pulse wave delay is visable as the slight phase difference between the two tracings. As the probes are at the same level, the pulse amplitudes are essentially identical. FIG. 23 shows the oscilloscope screen after the hand with the probe displayed as the top tracing has been placed at a level higher than the heart and the hand with the probe displayed as the bottom tracing has been placed at a level lower than the heart. The induction of a pressure differential between the two probes effects a change in the pulse delay. The change in pressure also correspondingly alters the pulse amplitudes. FIG. 24 shows the oscilloscope screen after the hand with the probe displayed as the top tracing has been placed at a level lower than the heart and the hand with the probe displayed as the bottom tracing has been placed at a level higher than the heart. Here, the pulse delay has substantially reversed as have the pulse amplitudes. FIG. 25 shows an oscilloscope screen displaying an electrocardiogram in conjunction with a pulse waveform.

The algorithms outlined below serve as examples, but modifications are possible to arrive at the indicated results, and are meant to be included within the spirit of this application. Various additional components of the device will be discussed in more detail below with reference to the following examplary determinations.

(d1). Determination of Arterial Blood Pressure

A probe such as that shown in FIG. 1 is placed on an extremity, and that extremity is moved in relation to the heart. As mentioned above, the hydrostatic pressure within the arteries and arterioles changes as a function of height with respect to the heart. Because of this, both the pulse wave velocity and pulse wave amplitude change as a function of probe height. These two parameters can be mapped against known distance above or below the heart. In this way, function curves of pressure vs. pulse wave amplitude and pressure vs. pulse wave velocity can be drawn. For example, a full excursion of the arm in a standing adult produces hydrostatic changes of greater than 50 cm of water in both directions. Using an arm and a leg, a gradient of well over 200 cm of water can be generated. This is a significant portion of the normal blood pressure range, and certainly enough to produce the function curves mentioned above.

There is a huge amount of medical literature describing arterial behavior, so the curves can be extrapolated if necessary. These curves serve as calibration.

It can thus be determined if "recalibration" is necessary—if either pulse amplitude or pulse wave velocity changes, and the other parameter does not change correspondingly. In other words, a shift on one curve should matched by a corresponding shift on the other curve. If this shift does not occur as predicted, recalibration is required. Of course, the process of recalibration is the simple procedure outlined above.

In a preferred embodiment, a first probe having a position sensor is placed level with the patient's heart. A second probe, such as one shown in FIG. 8, having a position sensor and a pulse detector is placed on the patient's finger. The patient's arm is held out level with the heart so there is zero displacement between probes. Pulse amplitude is recorded from probe. The patient's arm is slowly raised, while pulse amplitude and relative displacement of probe are recorded. The hydrostatic pressure difference between probes is also computed. By comparing the recorded pulse amplitude to the hydrostatic pressure difference, a mathematical function relating pressure to pulse amplitude can be derived. Preferably, circuitry similar to that shown in FIG. 13 is used to aid the process. This process is repeated while lowering the arm back to heart level, then lowering the arm to below heart level and, finally, raising the arm back to heart level. Similar steps can be applied to measure pulse delay, pulse velocity and pulse contour.

(d2). Determination of Cardiac Output

Cardiac output can be determined by measuring delays in pulse arrival times in coupled organs or members on opposite sides of the body. In a preferred embodiment of the invention, probes such as those shown in FIG. 1, having sensors for detecting a patient's pulse are placed on opposite fingers of the patient. The patient positions both arms straight out from the side. The blood pressure of the patient can be determined either through conventional means or by the methods of the invention. The pulse delay between the two probes can be measured utilizing circuitry such as that shown in FIG. 14 or 15, for example. The dicrotic notch of the pulse may be determined by standard methods, and used to calculate the ejection time based on the timing. The size of the aortic root can be estimated by standard means and the consequently the pulse distance differential at the aortic root. This allows the calculation of the pulse velocity c at the aortic route by the following equation:

$$c = (\text{pulse distance})/(\text{pulse delay}) \quad \text{Eq. 4}$$

The value of c can then be used to solve for flow wave velocity based on the following equation:

$$p = c*u*\rho \quad \text{Eq. 5}$$

Where:
c=pulse wave velocity;
u=flow wave velocity; and
$\rho$=density of the blood (approximately 1.055 grams/cm$^3$).

According to the invention, cardiac stroke volume can be determined by multiplying the aortic root area by the flow wave velocity and by the cardiac ejection time. Cardiac minute output can be calculated by multiplying the cardiac stroke volume by the pulse rate. These steps may be augmented by raising and lowering the patient's arms with respect to each other to vary the pressure and the pulse wave velocity.

Alternatively, cardiac output can be determined by placing probes such as those shown in FIG. 5 on a patient's finger and toe. The probes measure oxygen saturation at each pulse. The oxygen saturation for each pulse at the first probe is compared to the oxygen saturation of that pulse and subsequent pulses at the second probe. With continuous monitoring, this allows the determination matching oxygen saturation, within given tolerance limits, of the pulses from the probes. The patient's blood volume and the physical separation of the probes can be determined by standard methods. This allows the computation of caridac stroke volume by dividing the blood volume displaced by the number of pulses. Then, the cardiac minute output can be calculated by multiplying the cardiac stroke volume by pulse rate. Circuitry such as that shown in FIG. 11 or 12 is suitable for use with this embodiment.

(d3). Determination of Venous Saturation and Pressure

Determination of arterial oxygen saturation can be determined by pulse oximetry and techniques well delineated in both the patent and medical literature. Hydrostatic changes as described in this application allow the determination of venous saturation and pressure as well.

Place a probe such as that shown in FIG. 1 on a finger. Make measurements of both total absorbance and pulsatile absorbance. Raise the probe a known distance. Again measure both total absorbance and pulsatile absorbance. Both will be decreased. This is because the pulse amplitude is less because the arterial blood pressure within the probe is less (due to decrease in hydrostatic pressure). However, the total absorbance will also decrease, as the distending pressure in the venous system is less, and hence the veins and venules are smaller. All changes in absorbance can be assumed to be due to changes in blood volume. Saturation is calculated using the ratios of absorbance of distinct wavelengths.

In one embodiment, the central venous pressure (CVP) can be estimated. A probe containing a position sensor is place level with a patient's heart. A second probe, such as the one shown in FIG. 8, also comprising a position sensor is placed on the patient's finger. The patient positions the arm so that the second probe is initially lower than the first probe. The total absorbance measured at the second probe is continuously monitored. The patient's arm is slowly raised, and the rate of change of absorbance of the second probe is computed with respect to the relative displacement to the first probe. When the rate of change changes by a predetermined amount representing an abrupt decrease, the arm position corresponding to the point of central venous drainage has been reached. The CVP can then be calculated by computing the hydrostatic pressure difference between the first probe and the second probe at that arm position. The circuitry shown in FIG. 13 is suitable for use with this embodiment.

(d4). Determination of Heart Rate

According to the invention, heart rate can be determined by counting the pulsatile arterial signal for a known length of time, or by the ECG impulse.

(d5). Determination of Respiratory Rate

The impedance changes of the chest due to filling and emptying can be measured from the electrocardiogram tracing. During normal breathing, negative pressure is created within the chest by lowering of the diaphragm and expansion of the rib cage. This negative pressure causes blood to empty more rapidly from the peripheral into the central veins. This is also the case when respiration is assisted by a negative-pressure device such as the "iron lung".

During modern mechanically-assisted ventilation (with "ventilators"), positive pressure is created within the chest by forcing air into the lungs. For both positive- and negative-pressure ventilation, expiration is passive. This respiratory variation by itself can be used as an estimate of cardiac filling, giving left heart pressures. This determination can be assisted by the use of the hydrostatic techniques described above.

(d6). Diagnosis of Congenital Heart Disease and Anatomic Anomalies

Diagnosis of many disorders with anatomic anomalies can be made by the detection of unexpected propagation times, and abnormal propagation delays between right- and left-sided organs.

The ability to measure both arterial and venous saturation, as well as arterial and venous pressures, can aid further in investigations.

(d7). Diagnosis of Dysrhythmias

By measuring blood pressure and the electrocardiogram simultaneously, the diagnosis of dysrhythmias can be aided greatly. Both arterial and venous pressure are recorded with the ECG, allowing differentiation of atrial vs. ventricular arrhythmias.

(d8). Determination of Additional Cardiovascular Characteristics

By measuring blood pressure and the electrocardiogram simultaneously, many additional characteristics, such as systolic and diastolic pressure time indices, can be determined.

An enormous amount of information can be gleaned from the use of probes on opposite sides of the body combined with hydrostatic perturbations. It is important to realize that the time of arrival of a pulse to paired members is different, but the velocity of the pulse is also different. Examination of pulse propagation time, pulse propagation phase or delay, pulse velocity, and pulse amplitude yields four parameters that may change in different ways for each perturbation. Particularly, raising and lowering an arm by the same amount may give different changes. Raising and lowering the other arm by the same amount may give still different changes. Further, raising an arm by a given amount, then raising again by the same amount, may give different changes. Raising the other arm by the given amount, then raising again by the same amount, may give still different changes. Similar effects can be obtained by lowering the extremity.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for noninvasively determining a patient's cardiac output, comprising the steps of:
    providing a first tissue probe having a first radiation emitter and a first radiation detector, said first radiation emitter being adapted to emit first radiation having at least a first wavelength, said first radiation detector being adapted to receive said first radiation after absorbance through the patient's blood;
    providing a second tissue probe having a second radiation emitter and a second radiation detector, said second radiation emitter being adapted to emit second radiation having at least a second wavelength, said second radiation emitter being adapted to receive said second radiation after absorbance through the patient's blood, said first and second tissue probes being further adapted to measure the patient's blood pulse;
    placing said first tissue probe proximate a first extremity of the patient;
    placing said second tissue probe proximate a second, opposing extremity of the patient;
    substantially simultaneously and continuously measuring first extremity oxygen saturation at each blood pulse in said first extremity with said first tissue probe and second extremity oxygen saturation at each blood pulse in said second extremity with said second probe, said first extremity oxygen saturation measurement providing a plurality of first oxygen saturation values, said second extremity oxygen saturation measurement providing a plurality of second oxygen saturation values;
    measuring the patient's pulse rate;
    determining matching oxygen saturation using said first and second oxygen saturation values;
    determining the patient's blood volume:
    determining cardiac stroke volume using said blood volume and said pulse rate; and
    determining the patient's cardiac output using said cardiac stroke volume and said pulse rate.

2. The method of claim 1, including the steps of:
    determining pulse delay by comparing said first and second oxygen saturation values;
    estimating pulse distance differential;
    determining pulse wave velocity using said pulse distance differential and said pulse delay; and
    determining flow wave velocity using said pulse wave velocity.

3. The method of claim 2, further including the steps of estimating aortic root size and determining cardiac stroke volume using said flow wave velocity and said aortic root size.

4. The method of claim 3, further including the step of changing the position of said first and second tissue probes relative to a level corresponding to the patient's heart during said step of measuring said first extremity oxygen saturation and said second extremity oxygen saturation.

5. A method for noninvasively determining a patient's cardiac output, comprising the steps of:
    providing a first tissue probe having a first radiation emitter and a first radiation detector, said first radiation emitter being adapted to emit first radiation having at least a first wavelength, said first radiation detector being adapted to receive said first radiation after absorbance through the patient's blood;
    providing a second tissue probe having a second radiation emitter and a second radiation detector, said second radiation emitter being adapted to emit second radiation having at least a second wavelength, said second radiation emitter being adapted to receive said second radiation after absorbance through the patient's blood, said first and second tissue probes being further adapted to measure blood pulse delay;
    placing said first tissue probe proximate a first extremity of the patient;
    placing said second tissue probe proximate a second, opposing extremity of the patient;
    measuring a first time period between a first cardiac characteristic and a first detected pulse in said first extremity with said first tissue probe to determine a first blood pulse delay;
    measuring a second time period between a second cardiac characteristic and a second detected pulse in said second extremity with said second tissue probe to determine a second blood pulse delay;
    measuring the patient's pulse rate;
    estimating pulse distance differential;
    determining pulse wave velocity using said first and second blood pulse delays and said pulse distance differential;

determining flow wave velocity using said pulse wave velocity;

estimating aortic root size;

determining cardiac stroke volume using said flow wave velocity and said aortic root size; and determining the patient's cardiac output using said cardiac stroke volume and said pulse rate.

6. The method of claim 5, further including the step of changing the position of said first and second tissue probes relative to a level corresponding to the patient's heart to effect a change in said pulse wave velocity.

7. The method of claim 5, wherein said first and second cardiac characteristics comprise R-waves of an electrocardiogram.

8. A method for noninvasively determining a patient's cardiac output, comprising the steps of:

providing a first tissue probe having a first radiation emitter and a first radiation detector, said first radiation emitter being adapted to emit first radiation having at least a first wavelength, said first radiation detector being adapted to receive said first radiation after absorbance through the patient's blood;

providing a second tissue probe having a second radiation emitter and a second radiation detector, said second radiation emitter being adapted to emit second radiation having at least a second wavelength, said second radiation emitter being adapted to receive said second radiation after absorbance through the patient's blood, said first and second tissue probes being further adapted to measure blood pulse delay;

placing said first tissue probe proximate a first extremity of the patient;

placing said second tissue probe proximate a second, opposing extremity of the patient;

measuring a first time period between a first cardiac characteristic and a first detected pulse in said first extremity with said first tissue probe to determine a first blood pulse delay;

measuring a second time period between said first cardiac characteristic and said first detected pulse in said second extremity with said second tissue probe to determine a second blood pulse delay;

determining a blood pulse differential using said first and second blood pulse delays;

measuring the patient's pulse rate;

estimating pulse distance differential;

determining pulse wave velocity using said blood pulse differential and said pulse distance differential;

determining flow wave velocity using said pulse wave velocity;

estimating aortic root size;

determining cardiac stroke volume using said flow wave velocity and said aortic root size; and determining the patient's cardiac output using said cardiac stroke volume and said pulse rate.

9. The method of claim 8, further including the step of changing the position of said first and second tissue probes relative to a level corresponding to the patient's heart to effect a change in said pulse wave velocity.

10. The method of claim 8, wherein said first cardiac characteristic comprises an R-wave of an electrocardiogram.

* * * * *